United States Patent
Karve et al.

(10) Patent No.: US 12,370,262 B2
(45) Date of Patent: Jul. 29, 2025

(54) MESSENGER RNA VACCINES AND USES THEREOF

(71) Applicant: Translate Bio, Inc., Lexington, MA (US)

(72) Inventors: Shrirang Karve, Lexington, MA (US); Zarna Patel, Lexington, MA (US); Ashish Sarode, Lexington, MA (US); Yi Zhang, Lexington, MA (US); Frank DeRosa, Lexington, MA (US); Michael Heartlein, Lexington, MA (US)

(73) Assignee: Translate Bio, Inc., Lexington, MA (US)

(*) Notice: Subject to any disclaimer, the term of this patent is extended or adjusted under 35 U.S.C. 154(b) by 286 days.

(21) Appl. No.: 17/705,803

(22) Filed: Mar. 28, 2022

(65) Prior Publication Data

US 2022/0347307 A1    Nov. 3, 2022

Related U.S. Application Data

(63) Continuation of application No. 16/425,693, filed on May 29, 2019, now abandoned.

(60) Provisional application No. 62/678,225, filed on May 30, 2018.

(51) Int. Cl.
| | | |
|---|---|---|
| A61K 47/00 | (2006.01) | |
| A61K 31/7105 | (2006.01) | |
| A61K 47/54 | (2017.01) | |
| A61K 47/64 | (2017.01) | |
| A61K 47/69 | (2017.01) | |
| C12N 15/63 | (2006.01) | |
| C12N 15/85 | (2006.01) | |
| A61K 39/00 | (2006.01) | |

(52) U.S. Cl.
CPC ...... *A61K 47/6455* (2017.08); *A61K 31/7105* (2013.01); *A61K 47/555* (2017.08); *A61K 47/6929* (2017.08); *C12N 15/85* (2013.01); *A61K 2039/51* (2013.01)

(58) Field of Classification Search
None
See application file for complete search history.

(56) References Cited

U.S. PATENT DOCUMENTS

| | | |
|---|---|---|
| 4,373,071 A | 2/1983 | Itakura |
| 4,401,796 A | 8/1983 | Itakura |
| 4,415,732 A | 11/1983 | Caruthers et al. |
| 4,458,066 A | 7/1984 | Caruthers et al. |
| 4,500,707 A | 2/1985 | Caruthers et al. |
| 4,668,777 A | 5/1987 | Caruthers et al. |
| 4,689,338 A | 8/1987 | Gerster |
| 4,737,323 A | 4/1988 | Martin et al. |
| 4,973,679 A | 11/1990 | Caruthers et al. |
| 5,047,524 A | 9/1991 | Andrus et al. |
| 5,057,540 A | 10/1991 | Kensil et al. |
| 5,132,418 A | 7/1992 | Caruthers et al. |
| 5,153,319 A | 10/1992 | Caruthers et al. |
| 5,171,678 A | 12/1992 | Behr et al. |
| 5,238,944 A | 8/1993 | Wick et al. |
| 5,262,530 A | 11/1993 | Andrus et al. |
| 5,334,761 A | 8/1994 | Gebeyehu et al. |
| 5,650,398 A | 7/1997 | Kensil et al. |
| 5,700,642 A | 12/1997 | Monforte et al. |
| 5,744,335 A | 4/1998 | Wolff et al. |
| 5,885,613 A | 3/1999 | Holland et al. |
| 6,524,584 B2 | 2/2003 | Kensil et al. |
| 6,645,495 B1 | 11/2003 | Kensil et al. |
| 6,693,086 B1 | 2/2004 | Dow et al. |
| 8,093,367 B2 | 1/2012 | Kore et al. |
| 8,304,529 B2 | 11/2012 | Kore et al. |
| 9,629,804 B2 | 4/2017 | Heartlein et al. |
| 2012/0213814 A1 | 8/2012 | Shiratsuchi et al. |
| 2015/0110859 A1 | 4/2015 | Heartlein et al. |
| 2016/0038432 A1 | 2/2016 | Derosa et al. |
| 2016/0168207 A1 | 6/2016 | Kramps et al. |
| 2018/0153822 A1 | 6/2018 | Karve et al. |
| 2021/0186890 A1 | 6/2021 | Karve et al. |
| 2021/0187122 A1 | 6/2021 | Heartlein et al. |
| 2021/0206739 A1 | 7/2021 | Zhang et al. |
| 2021/0213140 A1 | 7/2021 | Zhang et al. |
| 2021/0220273 A1 | 7/2021 | Zhang et al. |
| 2022/0226244 A1 | 7/2022 | Zhang et al. |

FOREIGN PATENT DOCUMENTS

| | | |
|---|---|---|
| WO | 2005121348 A1 | 12/2005 |
| WO | 2010042877 A1 | 4/2010 |
| WO | 2010053572 A2 | 5/2010 |
| WO | 2010144740 A1 | 12/2010 |
| WO | 2012170889 A1 | 12/2012 |
| WO | 2013063468 A1 | 5/2013 |
| WO | 2013149140 A1 | 10/2013 |
| WO | WO 2014/152513 A1 | 9/2014 |

(Continued)

OTHER PUBLICATIONS

Richner et al., Cell, Mar. 2017, 168: 1114-1125.*
Alton, E. et al., "A randomised, double-blind, placebo-controlled trial of repeated nebulisation of non-viral cystic fibrosis transmembrane conductance regulator (CFTR) gene therapy in patients with cystic fibrosis," Efficacy and Mechanism Evaluation, Jul. 2016, vol. 3, No. 5, ISSN 2050-4365, 240 pages.
International Search Report and Written Opinion for PCT/US19/34474, 18 pages, (dated Sep. 10, 2019).
International Preliminary Report on Patentability for PCT/US19/34474, 8 pages, (dated Dec. 10, 2020).
Liang, F. et al., "Efficient Targeting and Activation of Antigen-Presenting Cells in Vivo after Modified mRNA Vaccine Administration in Rhesus Macaques", Molecular Therapy, vol. 25, No. 12, Dec. 1, 2017, pp. 1-13.

(Continued)

*Primary Examiner* — Ileana Popa
(74) *Attorney, Agent, or Firm* — MH2 Technology Law Group, LLP

(57) ABSTRACT

The present invention provides, among other things, methods and compositions of formulating nucleic acid-containing nanoparticles for efficient delivery of payload in vivo such that the method and compositions can be used to generate mRNA vaccines.

18 Claims, 6 Drawing Sheets

Specification includes a Sequence Listing.

(56) References Cited

FOREIGN PATENT DOCUMENTS

| WO | 2015061467 A1 | 4/2015 |
|---|---|---|
| WO | 2015095340 A1 | 6/2015 |
| WO | 2015184256 A2 | 12/2015 |
| WO | 2015199952 A1 | 12/2015 |
| WO | 2016004202 A1 | 1/2016 |
| WO | WO 2016/004318 A1 | 1/2016 |
| WO | 2016118724 A1 | 7/2016 |
| WO | 2016118725 A1 | 7/2016 |
| WO | 2016205691 A1 | 12/2016 |
| WO | 2017004143 A1 | 1/2017 |
| WO | 2017049245 A2 | 3/2017 |
| WO | 2017075531 A1 | 5/2017 |
| WO | 2017117528 A1 | 7/2017 |
| WO | 2017173054 A1 | 10/2017 |
| WO | WO 2018/078053 A1 | 5/2018 |
| WO | WO 2018/081459 A1 | 5/2018 |
| WO | WO 2018/089801 A1 | 5/2018 |
| WO | WO 2019/207060 A1 | 10/2019 |

OTHER PUBLICATIONS

Lutz, J. et al., "Unmodified mRNA in LNPs constitutes a competitive technology for prophylactic vaccines", NPJ Vaccines, vol. 2, No. 1, Oct. 19, 2017, pp. 1-9.

Magini, D. et al., "Self-Amplifying mRNA Vaccines Expressing Multiple Conserved Influenza Antigens Confer Protection against Homologous and Heterosubtypic Viral Challenge", PLOS One, vol. 11, No. 8, Aug. 15, 2016, pp. 1-25.

Oberli, M. et al., "Lipid Nanoparticle Assisted mRNA Delivery for Potent Cancer Immunotherapy", Nano Letters, vol. 17, No. 3, Mar. 8, 2017, pp. 1326-1335.

Pardi, N. et al., "Nucleoside modified mRNA vaccines induce potent T follicular helper and germinal center B cell response", The Journal of Experimental Medicine, vol. 215, No. 6, May 8, 2018, pp. 1571-1588.

Pardi, N. et al., "Zika virus protection by a single low-dose nucleoside-modified mRNA vaccination", Nature, vol. 543, No. 7644, Feb. 2, 2017, pp. 1-25.

Reichmuth, A. et al., "mRNA vaccine delivery using lipid nanoparticles", Therapeutic Delivery, vol. 7, No. 5, May 1, 2016, pp. 319-334.

Ahmad-Nejad et al., "Bacterial CpG-DNA and lipopolysaccharides activate Toll-like receptors at distinct cellular compartments," European Journal of Immunology, vol. 32, Issue 7, Jul. 2002, pp. 1958-1968.

Behr et al., "Efficient gene transfer into mammalian primary endocrine cells with lipopolyamine-coated DNA," Proceedings of the National Academy of Sciences USA, vol. 86, Sep. 1989, pp. 6982-6986.

Bloomfield, "Quasi-elastic light scattering applications in biochemistry and biology," Annual Review of Biophysics and Bioengineering, vol. 10, Jun. 1, 1981, pp. 421-450.

Budker et al., "Protein/Amphipathic Polyamine Complexes Enable Highly Efficient Transfection with Minimal Toxicity," BioTechniques, vol. 23, No. 1, Jul. 1997, pp. 139-147.

Chuang et al., "Toll-like receptor 9 mediates CpG-DNA signaling," Journal of Leukocyte Biology, vol. 71, Issue 3, Mar. 2002, pp. 538-544.

Derosa et al., U.S. Appl. No. 62/672,194, filed May 16, 2018 entitled "Ribose Cationic Lipids," 212 pages.

Derosa et al., U.S. Appl. No. 62/020,163, filed Jul. 2, 2014, entitled "Encapsulation of Messenger RNA," 53 pages.

Etz et al., "Identification of in vivo expressed vaccine candidate antigens from *Staphylococcus aureus*," PNAS, vol. 99, No. 10, May 14, 2002, pp. 6573-6578.

Fechter et al., "Recognition of mRNA cap structures by viral and cellular proteins," Journal of General Virology, vol. 86, 2005 (Published online ahead of print Feb. 10, 2005), pp. 1239-1249.

Felgner et al., "Lipofection: A highly efficient, lipid-mediated DNA-transfection procedure," Proceedings of the National Academy of Sciences USA, vol. 84, Nov. 1987, p. 7413-7417.

Gao et al., "A novel cationic liposome reagent for efficient transfection of mammalian cells," Biochemical and Biophysical Research Communications, vol. 179, Issue 1, Aug. 30, 1991, pp. 280-285.

Goodman-Snitkoff et al., "Roll of intrastructural/intermolecular help in immunization with peptide-phospholipid complexes," The Journal of Immunology, vol. 147, No. 2, Jul. 15, 1991, pp. 410-415 (7 pages total).

Grudzien et al., "Novel cap analogs for in vitro synthesis of mRNAs with high translational efficiency," RNA, vol. 10, No. 9, 2004, pp. 1479-1487.

Grudzien-Nogalska et al., "Phosphorothioate cap analogs stabilize mRNA and increase translational efficiency in mammalian cells," RNA, vol. 13, No. 10, 2007 (Published online Aug. 24, 2007), pp. 1745-1755.

Japanese Decision of Rejection, dated Jun. 25, 2024, for Japanese Application No. 2020-566618, including English translation, 8 pages.

Japanese Notice of Reasons for Rejection, dated Nov. 17, 2023, for Japanese Application No. 2020-566618, including English translation, 6 pages.

Japanese Notice of Reasons for Rejection, dated May 2, 2023, for Japanese Application No. 2020-566618, including English translation, 6 pages.

Heyes et al., "Cationic lipid saturation influences intracellular delivery of encapsulated nucleic acids," Journal of Controlled Release, vol. 107, 2005 (Available online Jul. 28, 2005), pp. 276-287.

Jemielity et al., "Novel 'anti-reverse' cap analogs with superior translational properties," RNA, vol. 9, No. 9, 2003, pp. 1108-1122.

Karve et al., U.S. Appl. No. 62/420,413, filed Nov. 11, 2016, entitled "Novel Lipid Nanoparticle Formations of mRNA," 86 pages.

Karve et al., U.S. Appl. No. 62/580,155, filed Nov. 1, 2017, entitled "Novel Lipid Nanoparticle Formulations of mRNA," 95 pages.

Klibanov et al., "Amphipathic polyethyleneglycols effectively prolong the circulation time of liposomes," FEBS Letters, vol. 268, No. 1, Jul. 30, 1990, pp. 235-237.

Lingnau et al., "Poly-L-arginine synergizes with oligodeoxynucleotides containing CpG-motifs (CpG-ODN) for enhanced and prolonged immune responses and prevents the CpG-ODN-induced systemic release of pro-inflammatory cytokines," Vaccine, vol. 20, Issues 29-30, Oct. 4, 2002, pp. 3498-3508.

Love et al., "Lipid-like materials for low-dose in vivo gene silencing," Proceedings of the National Academy of Sciences USA, vol. 107, No. 5, Feb. 2, 2010, pp. 1864-1869.

McClellan et al., "Genetic Heterogeneity in Human Disease," Cell, vol. 141, Apr. 16, 2010, pp. 210-217.

McSorley et al., "Bacterial flagellin is an effective adjuvant for $CD_4$+T cells in vivo," Journal of Immunology, vol. 169, No. 7, Oct. 1, 2002, pp. 3914-3919.

Morrissey et al., "Potent and persistent in vivo anti-HBV activity of chemically modified siRNAs," Nature Biotechnology, vol. 23, No. 8, Aug. 2005 (Published Jul. 24, 2005), pp. 1002-1007.

Schellack et al., "IC31, a novel adjuvant signaling via TLR9, induces potent cellular and humoral immune responses," Vaccine, vol. 24, Issue 26, Jun. 29, 2006 (Available online Apr. 7, 2006), pp. 5461-5472.

Semple et al., "Rational design of cationic lipids for siRNA delivery," Nature Biotechnology, vol. 28, No. 2, Feb. 2010 (Published online Jan. 17, 2010), pp. 172-176, XP002633693.

Veazey et al., "Use of a Small Molecule CCR5 Inhibitor in Macaques to Treat Simian Immunodeficiency Virus Infection or Prevent Simian-Human Immunodeficiency Virus Infection," The Journal of Experimental Medicine, vol. 198, No. 10, Nov. 17, 2003, pp. 1551-1562.

Whitehead et al., "Degradable Lipid Nanoparticles with Predictable In Vivo siRNA Delivery Activity," Nature Communications, vol. 5, No. 4277, Jun. 27, 2014 (Available in PMC Dec. 27, 2014), 10 pages.

Woo, Chem Chiuh (Dr.) (SG Authorized Officer), Singapore First Written Opinion, dated Jul. 27, 2022, for Singapore Application No. 11202011587, 9 pages.

(56) References Cited

OTHER PUBLICATIONS

Woo, Chem Chiuh (Dr.) (SG Authorized Officer), Singapore Second Written Opinion, dated Jan. 29, 2024, for Singapore Application No. 11202011587, 11 pages.

Chinese First Office Action and Search Report, dated Jun. 27, 2022, for Chinese Application No. 201980044654.5, including English translation, 25 pages.

Yokoe et al., "Spatial dynamics of GFP-tagged proteins investigated by local fluorescence enhancement," Nature Biotechnology, vol. 14, Oct. 1, 1996, pp. 1252-1256.

Zhang et al., U.S. Appl. No. 62/676,147 filed May 24, 2018 entitled "Thioester Cationic Lipids," 134 pages.

Zuber et al., "Topical delivery of imiquimod to a mouse model as a novel adjuvant for human immunodeficiency virus (HIV) DNA," Vaccine, vol. 22, Issues 13-14, Apr. 16, 2004, pp. 1791-1798.

\* cited by examiner

MESSENGER RNA VACCINES AND USES THEREOF

CROSS REFERENCE TO RELATED APPLICATIONS

This application is a continuation of U.S. patent application Ser. No. 16/425,693, filed on May 29, 2019, which claims benefit of U.S. Provisional Patent Application No. 62/678,225, filed on May 30, 2018, which is hereby incorporated by reference in its entirety.

INCORPORATION-BY-REFERENCE OF SEQUENCE LISTING

The present specification makes reference to a Sequence Listing submitted electronically as a .txt file named "MRT-2021US2_SL.txt" on Jul. 7, 2022, and is 1,219 bytes in size. The entire contents of the Sequence Listing are herein incorporated by reference in their entirety.

BACKGROUND

Vaccines are among the most important medicines for treating or preventing various diseases. A vaccine is a biological composition that induces active acquired immunity to a particular disease. Traditionally, a vaccine typically contains an agent that resembles a disease-causing microorganism and is often made from weakened or killed forms of a virus or other microbes, or its surface proteins. The agent stimulates the body's immune system to produce antibodies or cytokines to recognize and destroy any of the microorganisms associated with that agent that it may encounter in the future. Vaccines can be prophylactic or therapeutic.

SUMMARY OF INVENTION

The present invention provides an improved and unconventional form of vaccines based on messenger RNA delivery that promises safer, more efficacious and cost-effective vaccines for treating and preventing various diseases.

In one aspect, the present invention provides a method for inducing an immune response in vivo by administering to the subject a messenger RNA (mRNA) composition comprising an mRNA encoding an antigen, at a dosing regimen sufficient to induce an antigen specific T cell response and/or an antigen specific antibody response. In some embodiments, the mRNA is encapsulated in lipid nanoparticles (LNPs). In some embodiments, the composition is a vaccine composition.

In some embodiments, the composition is administered subcutaneously. In some embodiments, the composition is administered intradermally. In some embodiments, the composition is administered intramuscularly. In some embodiments, the composition is administered intravenously. In some embodiments, the composition is not administered intravenously.

In another aspect, the present invention provides a method of delivering a vaccine in vivo comprising administering to a subject a vaccine composition comprising an mRNA encoding an antigen, encapsulated in a LNP, and wherein the vaccine composition is administered intramuscularly or subcutaneously. In various embodiments, the vaccine composition is administered at a dosing regimen sufficient to induce an antigen specific T cell response and/or an antigen specific antibody response.

In some embodiments, an antigen encoded by the mRNA is a protein or a peptide.

In some embodiments, a composition comprising one or more than one mRNAs encoding one or more polypeptides is delivered.

In some embodiments, a suitable dosing regimen comprises injecting a single dose. In some embodiments, a suitable dosing regimen comprises administering multiple doses periodically.

In some embodiments, the single dose or multiple doses (individually or collectively) range from about 0.1 µg-100 mg mRNA. In some embodiments, the single dose or multiple doses (individually or collectively) range from about 0.1 µg-50 mg mRNA, from about 0.1 µg-25 mg mRNA, from about 0.1 µg-10 mg mRNA, from about 0.1 µg-5 mg mRNA, from about 0.1 µg-1 mg mRNA, or from about 0.1 µg-100 µg mRNA. In some embodiments, the single dose is or the multiple doses (individually or collectively) are selected from 0.1 µg. 0.3 µg, 0.5 µg, 1 µg, 5 µg, 10 µg, 25 µg, 50 µg, or 100 µg.

In some embodiments, the single dose or the multiple doses (individually or collectively) range from about 0.01 mg/kg-10 mg/kg (mRNA/body weight). In some embodiments, the single dose or the multiple doses (individually or collectively) range from about 0.01 µg/kg-8 mg/kg, from about 0.01 µg/kg-6 mg/kg, from about 0.01 µg/kg-5 mg/kg, from about 0.1 µg/kg-5 mg/kg, from about 0.1 µg/kg-1 mg/kg, or from about 0.1 µg/kg-0.5 mg/kg (mRNA/body weight).

In some embodiments, the multiple doses comprise the same individual dosage amount of mRNA. In some embodiments, the multiple doses comprise different individual dosage amount of mRNA.

In some embodiments, each of the multiple doses are injected 1-3 weeks apart. In some embodiments, each of the multiple doses is injected weekly. In some embodiments, at least two of the multiple doses are injected within 3 weeks. In some embodiments, the multiple doses are injected at the following schedule: Dose 1 on week 0, dose 2 on week 3, and dose 3 on week 5.

In some embodiments, the mRNA has a length of or greater than about 0.5 kb, 1 kb, 1.5 kb, 2 kb, 2.5 kb, 3 kb, 3.5 kb, 4 kb, 4.5 kb, 5 kb, 6kb, 7 kb, 8 kb, 9 kb, 10 kb, 11 kb, 12 kb, 13 kb, 14 kb, or 15 kb. In some embodiments, the mRNA comprises unmodified nucleotides. In some embodiments, the mRNA comprises one or more modified nucleotides. In some embodiments, the one or more modified nucleotides comprise pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 4'thiouridine, 4'-thiocytidine, and/or 2-thiocytidine.

In some embodiments, the mRNA comprises a 5' untranslated region (5' UTR) and/or a 3' untranslated region (3' UTR).

In some embodiments, the nanoparticle is a lipid-based or polymer-based nanoparticle. In some embodiments, the lipid-based nanoparticle is a liposome. In some embodiments, the lipid nanoparticle comprises one or more cationic lipids, one or more helper lipids, and/or one or more PEGylated lipids. In some embodiments, the lipid nanoparticle comprises one or more cationic lipids, one or more helper lipids, and one or more PEGylated lipids. In some embodiments, the lipid nanoparticle comprises one or more cationic lipids, one or more helper lipids, one or more cholesterol-based lipids, and one or more PEGylated lipids. As used herein, the terms "PEGylated lipids" and "PEG modified lipids" are used inter-changeably.

In some embodiments, the lipid nanoparticle comprises one or more PEGylated lipids. In some embodiments, the PEGylated lipids constitute at least 1%, at least 2%, at least 3%, at least 4%, at least 5%, at least 6%, at least 7%, at least 8%, at least 9%, or at least 10% of the total lipids in the lipid nanoparticle. In some embodiments, the PEGylated lipids constitute at least 5% of the total lipids in the lipid nanoparticle. In some embodiments, the PEGylated lipids constitute about 5% of the total lipids in the lipid nanoparticle. In some embodiments, the PEGylated lipids constitute 10% or less, 9% or less, 8% or less, 7% or less, 6% or less, 5% or less, 4% or less, or 3% or less of the total lipids in the lipid nanoparticle. In some embodiments, the PEGylated lipids constitute 5% or less of the total lipids in the lipid nanoparticle.

In some embodiments, the lipid nanoparticle comprises one or more cationic lipids. In some embodiments, the one or more cationic lipids are selected from the group consisting of cKK-E12, OF-02, C12-200, MC3, DLinDMA, DLinkC2DMA, ICE (Imidazol-based), HGT5000, HGT5001, HGT4003, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24), and combinations thereof. In some embodiments, the at least one cationic lipid is selected from CCBene, ICE, ML-2, C12-200 or DLin-SS-DMA. In some embodiments, the one or more cationic lipids comprise ICE. In some embodiments, the one or more cationic lipids comprise ML-2. In some embodiments, the one or more cationic lipids comprise CCBene.

In some embodiments, the lipid nanoparticle comprises one or more helper lipids. In some embodiments, the helper lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)).

In some embodiments, the lipid nanoparticle comprises one or more cholesterol-based lipids. In some embodiments, the cholesterol-based lipids are selected from DC-Choi (N,N-dimethyl—N-ethylcarboxamidocholesterol), 1,4-bis (3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE.

In some embodiments, the administration of the composition results in expression of the antigen encoded by mRNA in the lymph nodes of the subject. In some embodiments, the administration of the composition results in expression of the antigen encoded by mRNA in the lymphocytes of the subject.

In some embodiments, the administration of the composition results in an antigen specific antibody response. In some embodiments, the antigen specific antibody response is measured by the presence of antigen-specific antibodies in serum.

In some embodiments, the administration of the composition results in an antigen specific T-cell response. In some embodiments, the antigen specific T-cell response is measured by cytokine response. In some embodiments, the antigen specific T-cell response is measured by IFN-ϒ ELISPOT in splenocytes.

In some embodiments, the antigen specific antibody response and/or the antigen specific T-cell response is detectable at least 24 hours, 2 days, 3 days, 4 days, 5 days, 6 days, 1 week, 2 weeks, 3 weeks, 4 weeks, or 1 month post-administration.

An aspect of the invention provides a method of treating a disease, disorder or condition comprising delivering messenger RNA (mRNA) to a subject in need of treatment according to the methods described above.

In this application, the use of "or" means "and/or" unless stated otherwise. As used in this disclosure, the term "comprise" and variations of the term, such as "comprising" and "comprises," are not intended to exclude other additives, components, integers or steps. As used in this application, the terms "about" and "approximately" are used as equivalents. Both terms are meant to cover any normal fluctuations appreciated by one of ordinary skill in the relevant art.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF FIGURES

The drawings are for illustration purposes, not for limitation.

DEFINITIONS

Figure 1:
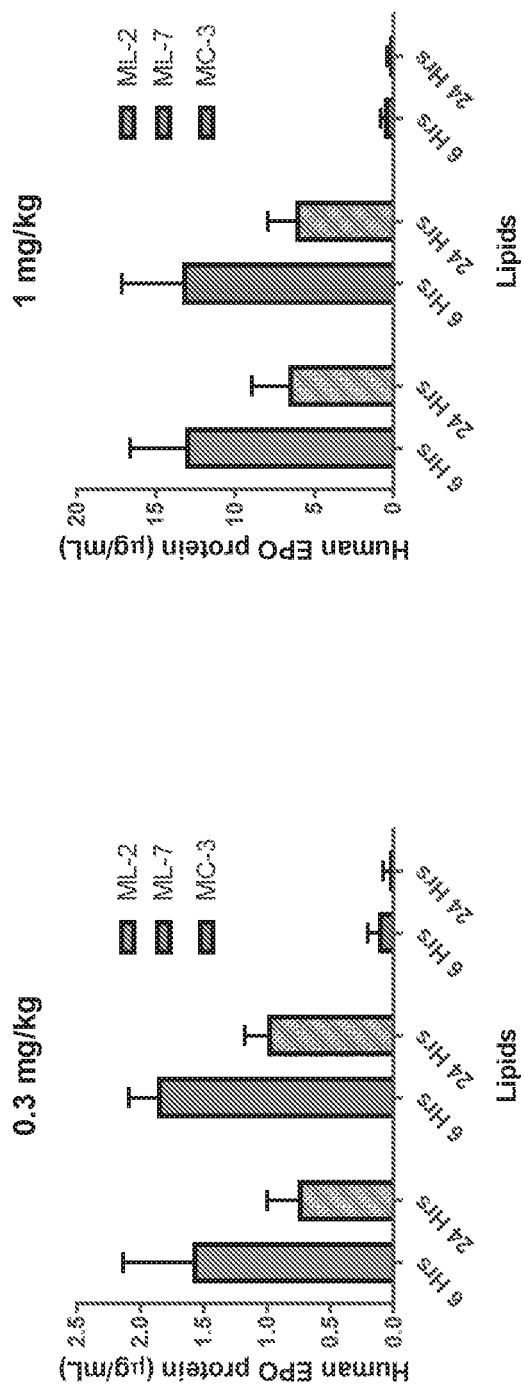
FIGS. 1A and B depicts comparison data on efficacy of three different lipid compositions in in vivo human erythropoietin (hEPO) mRNA delivery, as indicated by measuring hEPO protein in the serum.

In order for the present invention to be more readily understood, certain terms are first defined below. Additional definitions for the following terms and other terms are set forth throughout the specification.

Adjuvant: As used herein, the term "adjuvant" refers to a substance or vehicle that non-specifically enhances the immune response to an antigen.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antigen: As used herein, an antigen is a protein or a peptide that induces an immune response, and the antigen is encoded by the mRNA administered. In general, an antigen is a foreign body which elicits an immune response. In such circumstances, an antigen may be proteinaceous in nature, but could also be a non-protein entity, such as a toxin, a small molecule, or a nucleic acid. For the purpose of the discussion herein, an antigen refers to a protein, a peptide or a polypeptide encoded by mRNA administered, which elicits or is expected to elicit an immune response is the antigen.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Encapsulation: As used herein, the term "encapsulation," or grammatical equivalent, refers to the process of confining an individual mRNA molecule within a nanoparticle.

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

Messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Subcutaneous administration: As used herein, the term "subcutaneous administration" or "subcutaneous injection" refers to a bolus injection into the subcutis which is the tissue layer between the skin and the muscle.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Vaccination: As used herein, the term "vaccination" refers to the administration of a composition intended to generate an immune response, for example an mRNA encoding an antigen (e.g., a component of a disease-causing agent). For the purposes of the present invention, vaccination can be administered before, during, and/or after exposure to a disease-causing agent, and in some embodiments, before, during, and/or shortly after exposure to the agent. In some embodiments, vaccination includes multiple administrations, appropriately spaced in time, of a vaccinating composition.

DETAILED DESCRIPTION

The present invention provides, among other things, improved methods and compositions for mRNA vaccine delivery.

Various aspects of the invention are described in detail in the following sections. The use of sections is not meant to limit the invention. Each section can apply to any aspect of the invention. In this application, the use of "or" means "and/or" unless stated otherwise.

In one aspect of the invention, a method for inducing an immune response in a subject is provided. The method comprises administering a composition comprising an mRNA encoding an antigen at a dosing regimen sufficient to induce an antigen-specific T cell response or antigen-specific antibody response. In some embodiments, the composition is administered subcutaneously. In some embodiments, the composition is administered intradermally. In some embodiments, the composition is administered intramuscularly.

In one aspect of the invention, a method for delivering a vaccine in vivo is provided. The method comprises administering to a subject in need thereof a vaccine comprising an mRNA encoding an antigen encapsulated in a lipid nanoparticle. In some embodiments, the composition is administered subcutaneously. In some embodiments, the composition is administered intradermally. In some embodiments, the composition is administered intramuscularly.

Messenger RNA (mRNA) Vaccines mRNA vaccines are novel and offer many advantages over present cell-based vaccines using live, attenuated or killed pathogen or toxoid vaccines. In addition to the safety, mRNA vaccines are cost-effective and provide flexible design platform. mRNA encoding an antigen could be directed to induce specific immune response, and therefore can be applied in developing a wide range of therapeutic and prophylactic mRNA vaccines for a wide variety of diseases, including infections and cancers.

Vaccines Against Infections

Vaccine candidates are well established for a large number of infectious pathogens. Typically, vaccines are agents that mimic at least in part a disease causing agent and thereby elicit an immune response by the mammalian host. In general vaccines are biological agents, such as heat killed, irradiated or otherwise attenuated pathogenic organisms, live attenuated microbes, protein or peptide antigens, conjugated antigens, toxins or microbial surface proteins or fragments thereof. However, an mRNA encoding a protein or a peptide antigen, is a safe and effective way to induce an immune response against the disease. As discussed above, mRNA can be effectively delivered to express in vivo by encapsulated in a liposome comprising suitable lipids discussed in a later section. This mRNA encoding the antigenic peptide or protein could therefore be used to generate the vaccine in vivo. An immune response generated by the mammalian host against the vaccine component is intended in turn to protect the host from a subsequent attack by the pathogen, since the immune system of the host is primed for the attack by the pathogen. In other words the host system has immunological memory (a component of the adaptive immune response) of the pathogen. This process is known as prophylactic vaccination. Additionally, a vaccine may boost the host's immune system in an existing infection, for example by redirect an immune response against new and less recognized microbial antigen(s) (subdominant antigens) which then induce a strong immune response leading to pathogen elimination. This type of vaccine response may be categorized as therapeutic vaccination.

An immune response against a pathogen can be broken down into a few stages. First, an encounter of the human body (or a mammalian system) with a new pathogen, especially by contact through exposed surfaces such as skin or the internal mucosal surfaces of the respiratory, gastrointestinal, and urogenital tracts, lead to a non-specific innate immune response through activation of pattern recognition molecules. Pattern recognition molecules include a variety of germline-encoded receptors specialized in discriminating between microbial and host cell surfaces, or infected and normal cells. Phagocytes (monocytes, macrophages and dendritic cells), express pattern recognition molecules on their surface and are primarily responsible for recognizing, killing and elimination of the pathogens in an innate immune response. In doing so, phagocytes also process and present antigens to the circulating lymphocytes for generating a more specific antigen-targeted immune response, also known as the adaptive immune response. At this stage activated lymphocytes mature in the lymph nodes into antigen-specific T-cells expressing receptors for recognition of the antigen such that effector cytotoxic T cells recognize and kill a cell expressing the antigen when present in association with a second set of cell-surface molecules, the Major Histocompatibility Complex molecules or MHC; and helper T cells activate the system to generate the T cell memory and the humoral immune response. The humoral immune response comprises antibody-secreting B cells generated by clonal expression and differentiation over the course of several days, during which time that innate immunity continues to function. Clonal expansion of cytotoxic T cells also occur rapidly in lymphoid organs, such as lymph nodes and is augmented by exposure to antigens. Activated T cells generate a number cytokines, such as Interferon Gamma (IFN-γ) and Tumor Necrosis Factor alpha (TNF-α) which are considered the hallmarks of T cell activation. Eventually, antigen-specific T cells and then antibodies are released into the blood and recruited to the site of infection. A successful vaccine generates a rapid and robust cytotoxic T cell response, a strong antibody response and a lasting immunological memory.

Cancer Vaccines

Cancer is considered an immunological disease, and cancer immunotherapy has become the center-stage of research and development of the present day. In cancer immunotherapy, vaccines are developed to boost the immune system to turn against cancer antigens and eliminate a tumor by activated cytotoxic T cells directed against the antigens. One class of cancer antigens are viral antigens relating to the cancer-causing viruses, for example, Epstein Barr Virus (EBV) antigens such as EBV1 and EBV2 associated with lymphoma and nasopharyngeal carcinoma, Human Papilloma Virus (HPV) antigens such as HPV16 associated with cervical cancer (CC), Hepatitis B Virus (HBV) antigens and Hepatitis C Virus (HCV) antigens associated with hepatocellular carcinoma (HCC), human T lymphotropic virus type 1 (HTLV-1) associated with adult T-cell leukemia/lymphoma, and human herpes virus 8 (HHV-8) with Kaposi sarcoma, to name a few.

On the other hand, cancerous cells express antigens that are not commonly expressed by non-cancerous cells or tissues. Such antigens include but are not limited to epithelial tumor antigen (ETA) found in breast cancer, RAS family member p-53 and other activated RAS antigens, ovarian cancer antigens BRCA1 and BRCA2, melanoma associated antigen (MAGE) found in malignant melanoma cells, BCR-ABL fusion gene product found in myeloid leukemia, acute lymphoblastic leukemia, acute myelogenic leukemia, BRAF antigens found in cutaneous melanoma and colorectal cancer, epithelial growth factor receptor (EGFR) for non-small cell lung cancer, KRAS found in colorectal and non-small cell lung cancer, Neuron specific enolase, found in neuroblastoma and non-small cell lung cancer, NY-ESO 1 found in neuroblastoma, Melanoma-associated antigen recognized by T cells (MART-1) found in melanoma, programmed death ligand 1 (PD-L1) found in non-small cell lung cancer, Prostate-specific antigen (PSA) found in prostate cancer, urokinase plasminogen activator (UPA), plasminogen activator inhibitor (PAI-1) found in breast cancer, and many others, almost all of which are mutated endogenous proteins. These cancer antigens, being endogenous are not presented by antigen presenting cells (APCs) in a manner similar to viral antigens, i.e. in association with the MHC-1 molecule categorizing the antigen as foreign, but cytotoxic T cells are able to differentiate and identify mutated self-antigens and possess an inherent property to seek and destroy cells that bear the mutated antigens. Therefore, the current objective of cancer immunotherapy is to achieve optimum activation of cytotoxic T cells directed against the mutated antigens. A patient's specific mutations associated with her/his cancer can be mapped and used to generate vaccines, inducing the patient's own cytotoxic T cells to generate the necessary immune response to destroy tumor cells. mRNA vaccines could be the safe and cost-effective alternative to peptide vaccines for enabling such personalized medicine. Pan-genomic scanning and analysis of mutations present in a cancer patient could be used to specifically design mRNA encoding an antigen or epitope containing the mutation, which when administered in vivo will produce the translated product on a cell surface. This would direct an immune response against the mutated antigen. In the process, cytotoxic T cells attack the tumor cells, which inherently express the mutated antigen. Methods and protocols involved in executing pan genomic sequencing analysis, mutation analysis, epitope mapping and analysis and designing suitable peptides for vaccination are known to one of skill in the art.

This approach could also be leveraged to find dominant and subdominant antigens in a patient. It has been observed that both in chronic infection and cancer, certain antigens play a dominant role in producing an initial immune response. But soon afterwards, tolerance against such dominant antigens sets in, thereby the immune response is dampened. Genomic analysis and identification of antigens which did not show an initial dominant antigenic response (often termed subdominant antigens) could now be used to generate new and revived immune response.

One advantage of mRNA vaccines over peptide vaccines is that mRNA vaccines bypass the HLA-matching for the receiving host.

In a synthetic approach to mRNA vaccine design, a pathogen proteome can be scanned for antigenic signatures with vaccine potential. (Proteome database can be accessed using Uniprot Consortium, http://www.uniprot.org/). This could be effective in new pathogens, such as Zika virus. This type of reverse vaccinology has been employed in identifying a number of novel peptide vaccine candidates. New peptide vaccines were also identified from *Helicobacter pylori* and *Mycobacterium tuberculosis* by combining genomics and proteomics (See, for example, Etz et al., PNAS. 2002, 99 (10) 6573-6578). Whether the potential antigenic candidate can generate successful immune response can be verified by suitably expressing a library of potential antigens by various forms of cell surface display and subjecting to testing opsonization and antibody binding. Exemplary useful databases for vaccine antigen development include: ImMunoGeneTics information system (URL: www.imgt.org); Epitome Database, (URL: www.rostlab.org/services/epitome), Immune Epitope Database and Analysis Resource, www.iedb.org; Immunet database, immunet.cn/ced/index.php; HIV database: www.hiv.lanl.gov/content/immunology for immunogenetics and immunoinformatics.

Therefore, from the above discussion, it is clear that enrichment of mRNA vaccine delivery to lymph nodes can lead to access of the vaccines to both activated and naïve lymphocytes for lymphoproliferation and antigen-specific T cell and B cell generation. This localization of antigen activation is also less toxic as opposed to widespread immune activation.

Messenger RNA (mRNA)

The present invention may be used to deliver any mRNA encoding an antigen suitable for use as vaccines described herein. As used herein, mRNA is the type of RNA that carries information from DNA to the ribosome for translation of the encoded protein. mRNAs may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, in vitro synthesized mRNA may be purified before formulation and encapsulation to remove undesirable impurities including various enzymes and other reagents used during mRNA synthesis.

The present invention may be used to deliver mRNAs of a variety of lengths. In some embodiments, the present invention may be used to deliver in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to deliver in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

The present invention may be used to deliver mRNA that is unmodified or mRNA containing one or more modifications that typically enhance stability. In some embodiments, modifications are selected from modified nucleotides, modified sugar phosphate backbones, and 5' and/or 3' untranslated region (UTR).

In some embodiments, modifications of mRNA may include modifications of the nucleotides of the RNA. A modified mRNA according to the invention can include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydrouracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

In some embodiments, mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'-5' inverted triphosphate linkage; and the 7-nitrogen of guanine is then methylated by a methyltransferase. 2'-O-methylation may also occur at the first base and/or second base following the 7-methyl guanosine triphosphate residues. Examples of cap structures include, but are not limited to, m7GpppNp-RNA, m7GpppNmp-RNA and m7GpppNmpNmp-RNA (where m indicates 2'-Omethyl residues).

In some embodiments, mRNAs include a 3' poly(A) tail structure. A poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'-5'inverted triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("m$^7$GpppG") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH$_3$.

Additional cap analogs include, but are not limited to, a chemical structures selected from the group consisting of $m^7$GpppG, $m^7$GpppA, $m^7$GpppC; unmethylated cap analogs (e.g., GpppG); dimethylated cap analog (e.g., $m^{2,7}$GpppG), trimethylated cap analog (e.g., $m^{2,2,7}$GpppG), dimethylated symmetrical cap analogs (e.g., $m^7$Gpppm$^7$G), or anti reverse cap analogs (e.g., ARCA; $m^7$, $^{2'Ome}$GpppG, $m^{72'd}$GpppG, $m^{7,3'Ome}$GpppG, $m^{7,3'd}$GpppG and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("m$^7$G") linked via a triphosphate bridge to the 5'-end of the first transcribed nucleotide, resulting in m$^7$G (5')ppp(5')N, where N is any nucleoside. A preferred embodiment of a m$^7$G cap utilized in embodiments of the invention is m$^7$G(5')ppp(5')G.

In some embodiments, the cap is a CapO structure. CapO structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m$^7$G cap analogs are known in the art, many of which are commercially available. These include the m$^7$GpppG described above, as well as the ARCA 3'—OCH$_3$ and 2'—OCH$_3$ cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' tail structure. Typically, a tail structure includes a poly(A) and/or poly(C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly-A or poly-C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly(A) and poly(C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region (UTR)

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

While mRNA provided from in vitro transcription reactions may be desirable in some embodiments, other sources of mRNA are contemplated as within the scope of the invention including mRNA produced from bacteria, fungi, plants, and/or animals.

The present invention may be used to deliver mRNAs encoding a variety of proteins. Non-limiting examples of mRNAs suitable for the present invention include mRNAs encoding peptide or protein vaccines.

Exemplary mRNA Sequences

In some embodiments, the present invention provides methods and compositions for delivering mRNA encoding a target protein to a subject for the treatment of the target protein deficiency. Exemplary mRNA sequences are shown below.

Construct Design:

X-mRNA coding sequence-Y

5' and 3' UTR Sequences

```
X (5' UTR Sequence) =
                                          (SEQ ID NO: 1)
GGACAGAUCGCCUGGAGACGCCAUCCACGCUGUUUUGACCUCCAUAGAA
GACACCGGGACCGAUCCAGCCUCCGCGGCCGGGAACGGUGCAUUGGAAC
GCGGAUUCCCCGUGCCAAGAGUGACUCACCGUCCUUGACACG Y (3' UTR Sequence) =
                                          (SEQ ID NO: 2)
CGGGUGGCAUCCCUGUGACCCCUCCCCAGUGCCUCUCCUGGCCCUGGAA
GUUGCCACUCCAGUGCCCACCAGCCUUGUCCUAAUAAAAUUAAGUUGCA
UCAAGCU
OR
                                          (SEQ ID NO: 3)
GGGUGGCAUCCCUGUGACCCCUCCCCAGUGCCUCUCCUGGCCCUGGAAG
UUGCCACUCCAGUGCCCACCAGCCUUGUCCUAAUAAAAUUAAGUUGCAU
CAAAGCU
```

In some embodiments, a suitable mRNA encodes a fusion protein comprising a full length, fragment or portion of a target protein fused to another protein (e.g., an N or C terminal fusion). In some embodiments, the protein fused to the mRNA encoding a full length, fragment or portion of a target protein encodes a signal or a cellular targeting sequence.

Lipid Nanoparticles

According to the present invention, mRNA may be encapsulated or complexed in nanoparticles. In some embodiments, nanoparticles are also referred to as "delivery vehicle," "transfer vehicle", or grammatical equivalents.

According to various embodiments, suitable nanoparticles include, but are not limited to polymer based carriers, such as polyethylenimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic poly-conjugates), dry powder formulations, plasmids, viruses, calcium phosphate nucleotides, aptamers, peptides and other vectorial tags.

In some embodiments, the mRNA is encapsulated within one or more liposomes. As used herein, the term "liposome" refers to any lamellar, multilamellar, or solid nanoparticle vesicle. Typically, a liposome as used herein can be formed by mixing one or more lipids or by mixing one or more lipids and polymer(s). Thus, the term "liposome" as used herein encompasses both lipid and polymer based nanoparticles. In some embodiments, a liposome suitable for the present invention contains cationic, non-cationic lipid(s), cholesterol-based lipid(s) and/or PEG-modified lipid(s).

PEGylated Lipids

In some embodiments, a suitable lipid solution includes one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl (Methoxy Polyethylene Glycol)-2000] (C8 PEG-2000 ceramide) is also contemplated by the present invention. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. In some embodiments, particularly useful exchangeable lipids are PEG-ceramides having shorter acyl chains (e.g., $C_{14}$ or $C_{18}$).

PEG-modified phospholipid and derivatized lipids may constitute at least 1%, at least 2%, at least 3%, at least 4%, at least 5%, at least 6%, at least 7%, at least 8%, at least 9%, or at least 10% of the total lipids in the liposome.

Cationic Lipids

As used herein, the term "cationic lipids" refers to any of a number of lipid and lipidoid species that have a net positive charge at a selected pH, such as at physiological pH. Several cationic lipids have been described in the literature, many of which are commercially available.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

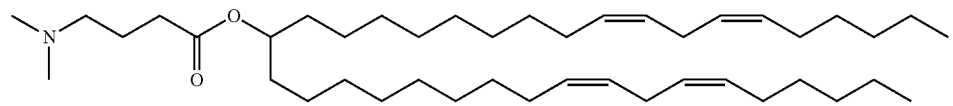 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

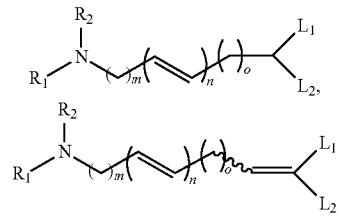

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)-N,N-dimethyl-6-(9Z,12Z)-octadeca-9,12-dien-1-yl) tetracosa-15,18-dien-1-amine ("HGT5000"), having a compound structure of:

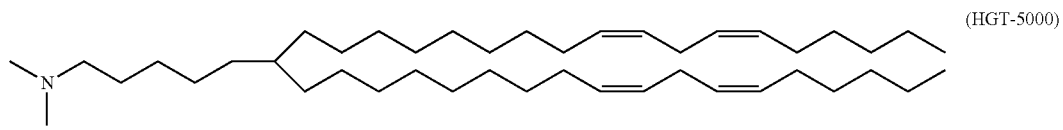 [SMILES: CCCCC/C=C\C/C=C\CCCCCCCCC(CCCCCCCC/C=C\C/C=C\CCCCC)CCCCCN(C)C]

(HGT-5000)

and pharmaceutically acceptable salts thereof. In certain embodiments, the compositions and methods of the present invention include the cationic lipid (15Z, 18Z)-N,N-dimethyl-6-((9Z,12Z)-octadeca-9,12-dien-1-yl) tetracosa-4,15,18-trien-1-amine ("HGT5001"), having a compound structure of:

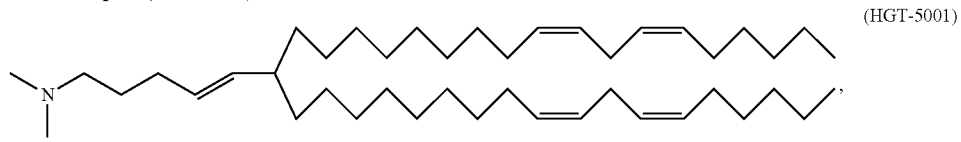
(HGT-5001)

and pharmaceutically acceptable salts thereof. In certain embodiments, the compositions and methods of the present invention include the cationic lipid and (15Z,18Z)-N,N-dimethyl-6-((9Z,12Z)-octadeca-9,12-dien-1-yl) tetracosa-5,15,18-trien-1-amine ("HGT5002"), having a compound structure of:

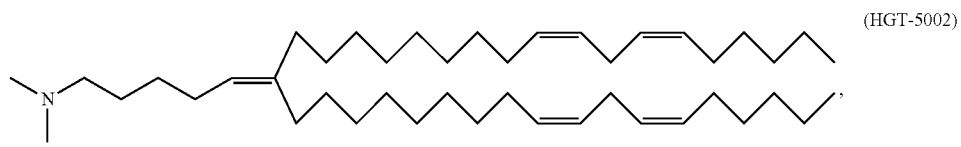 [SMILES: CCCCC/C=C\C/C=C\CCCCCCCCC(=CCCCCN(C)C)CCCCCCCC/C=C\C/C=C\CCCCC]
(HGT-5002)

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

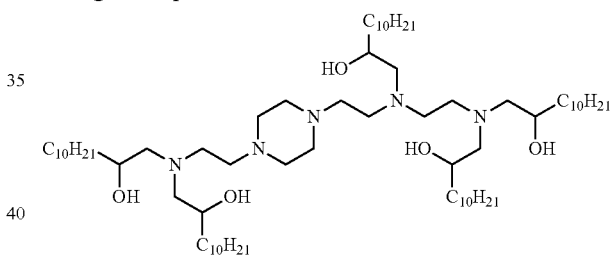

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

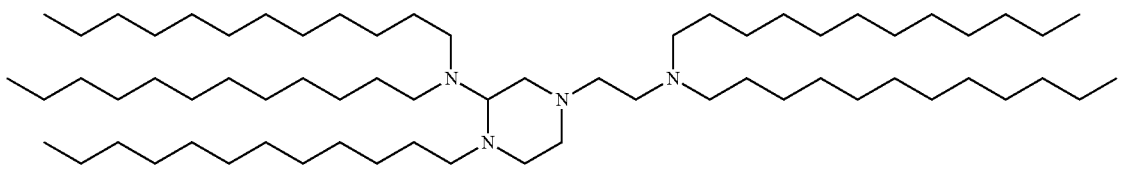 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

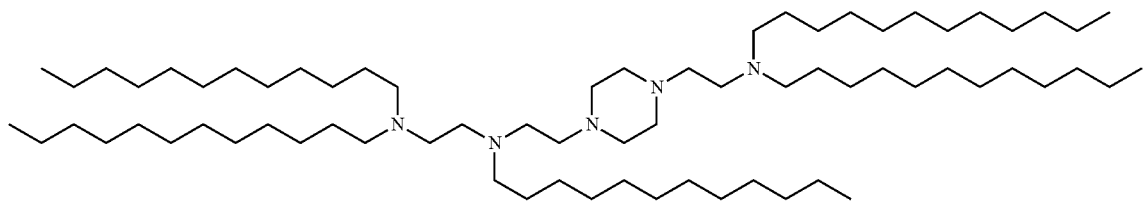 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

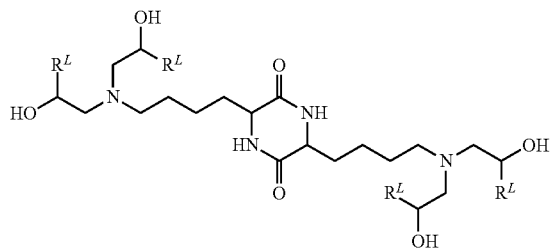

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

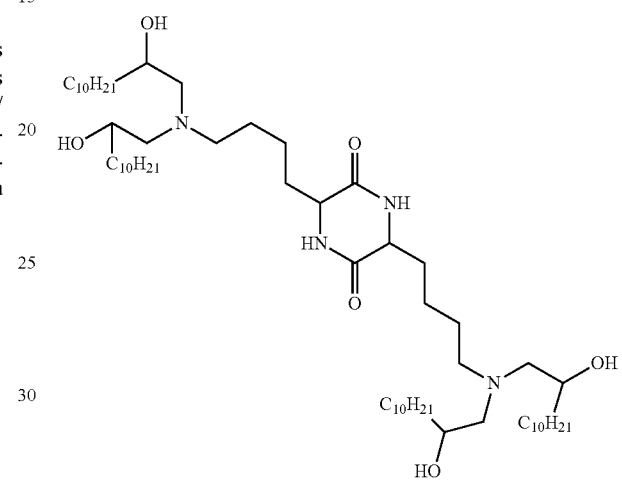

and pharmaceutically acceptable salts thereof. In certain embodiments, the compositions and methods of the present invention include a cationic lipid having a compound structure of:

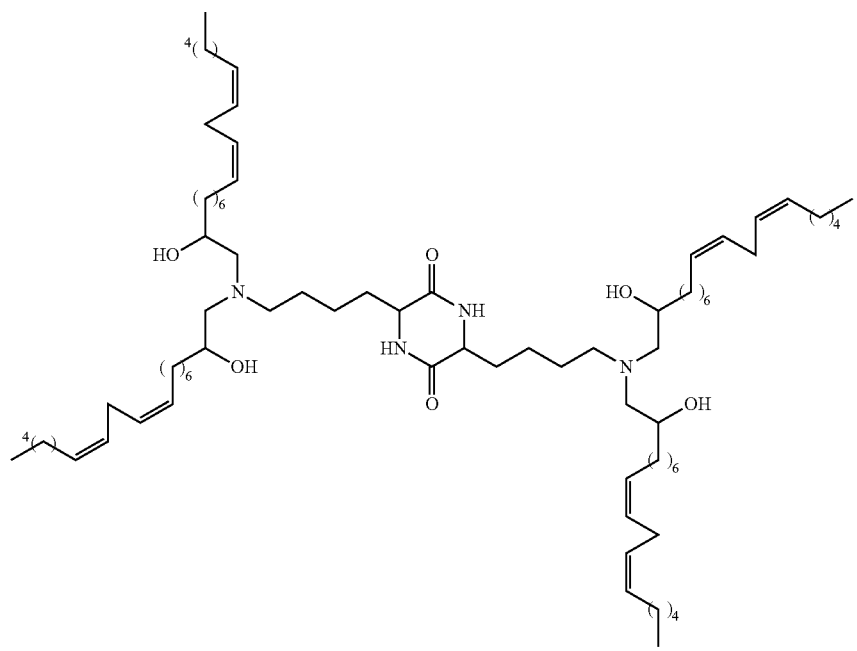

and pharmaceutically acceptable salts thereof. In certain embodiments, the compositions and methods of the present invention include a cationic lipid having a compound structure of:

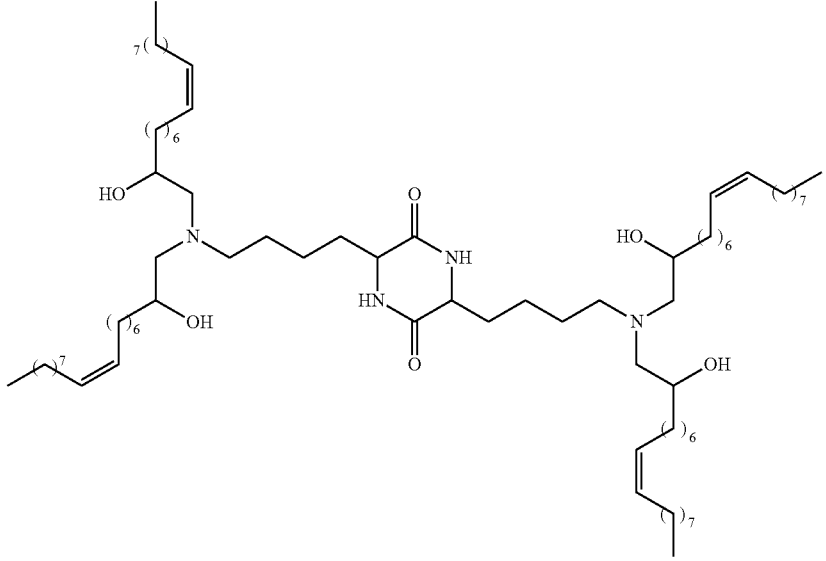

and pharmaceutically acceptable salts thereof. In certain embodiments, the compositions and methods of the present invention include a cationic lipid having a compound structure of:

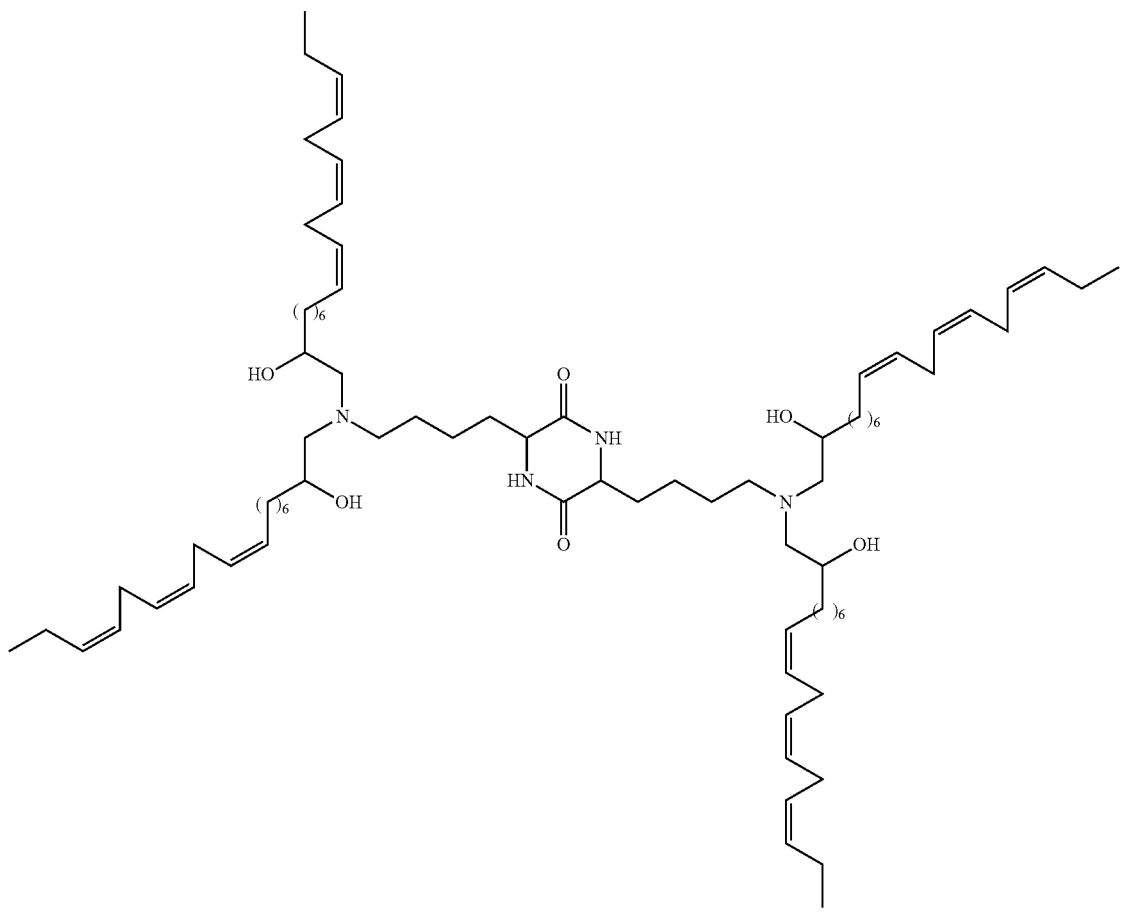

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

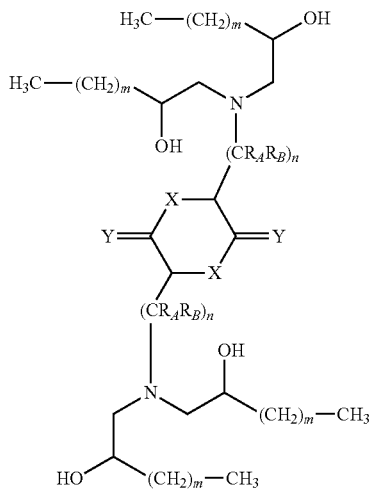

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

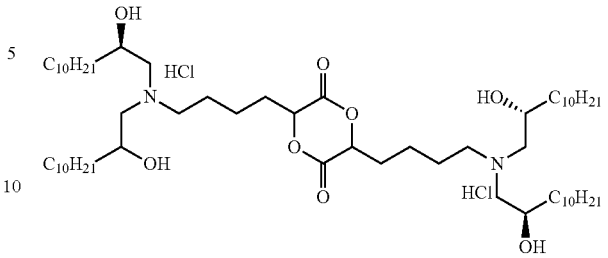

(Target 23)

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

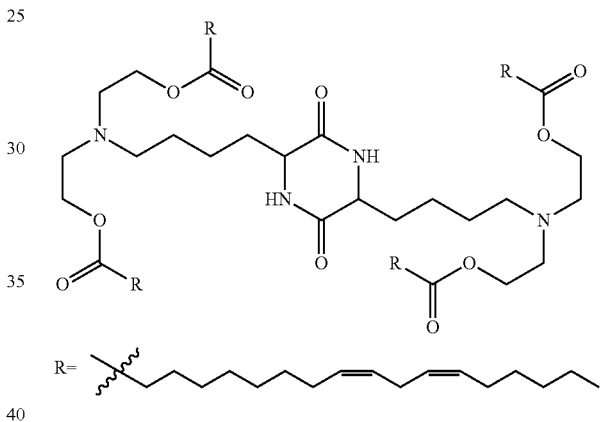

or a pharmaceutically acceptable salt thereof. In some embodiments, the compositions and methods of the present invention include a cationic lipid having the compound structure:

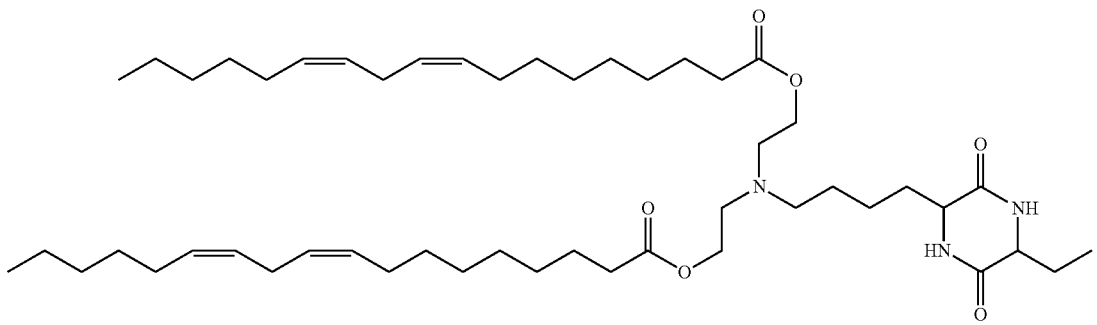 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

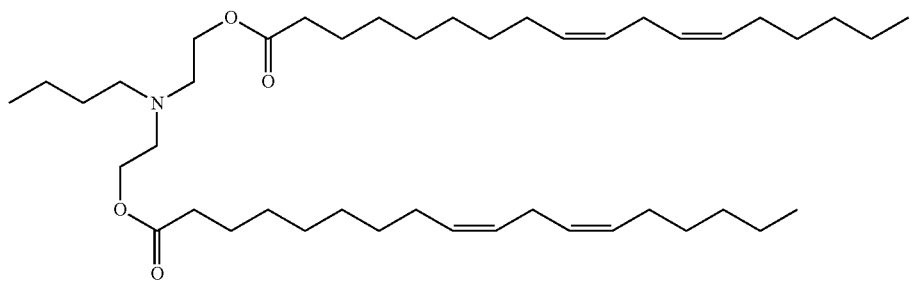 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

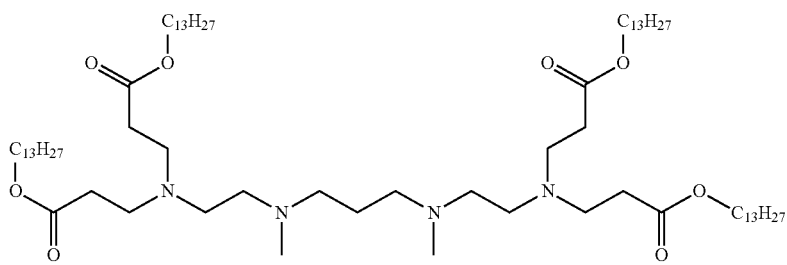

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

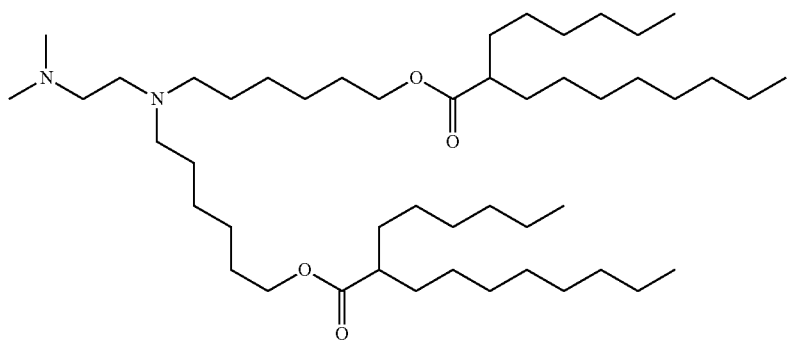 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

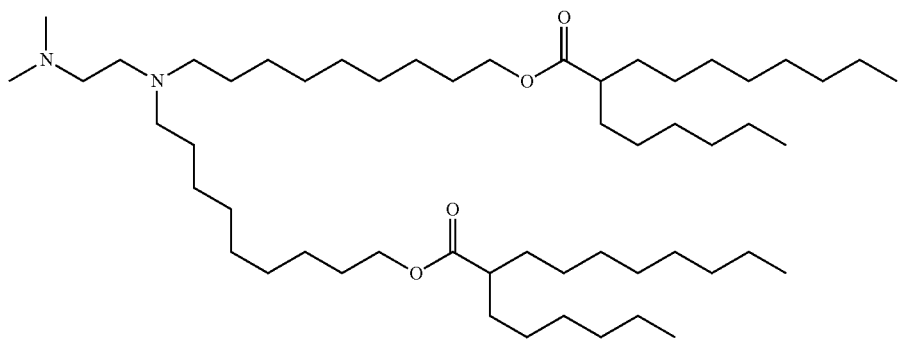 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

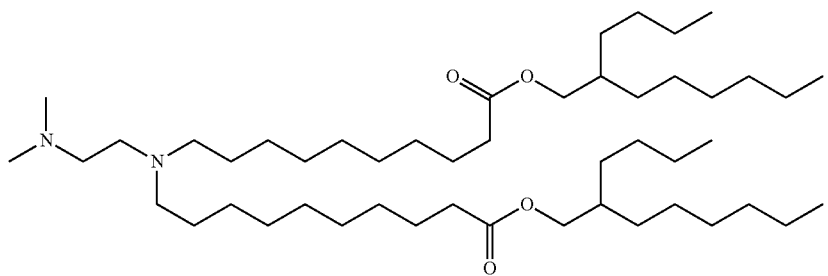 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

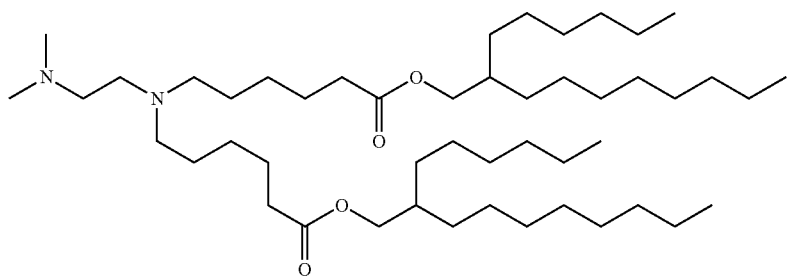 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

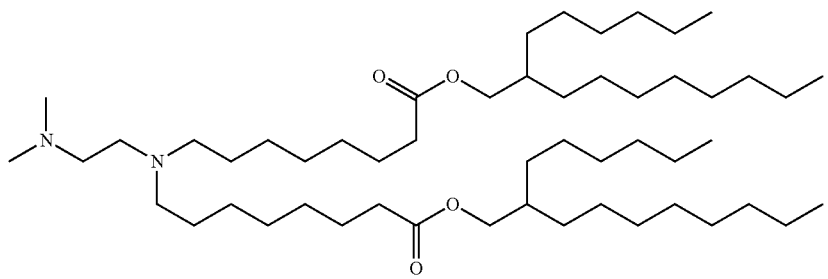 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

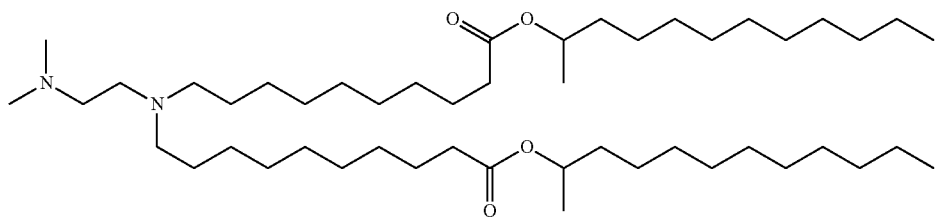 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

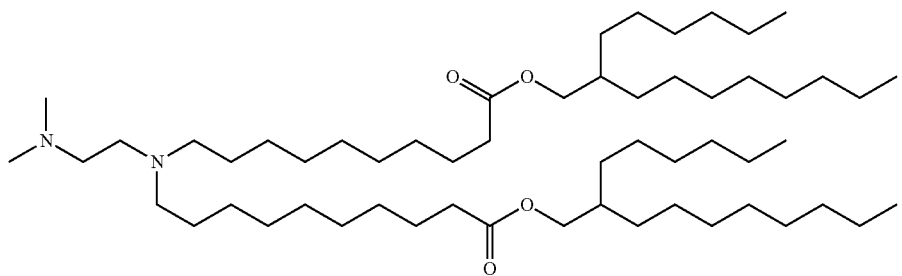 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

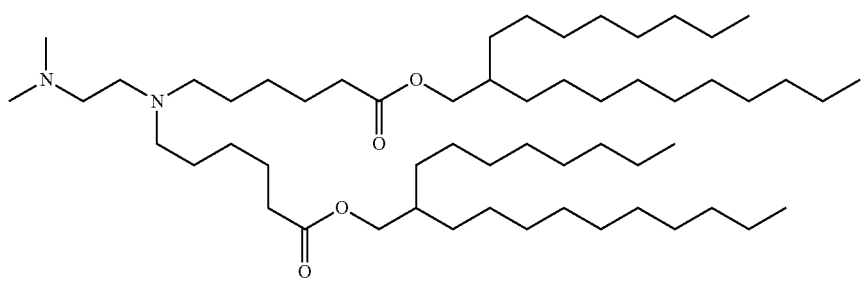 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

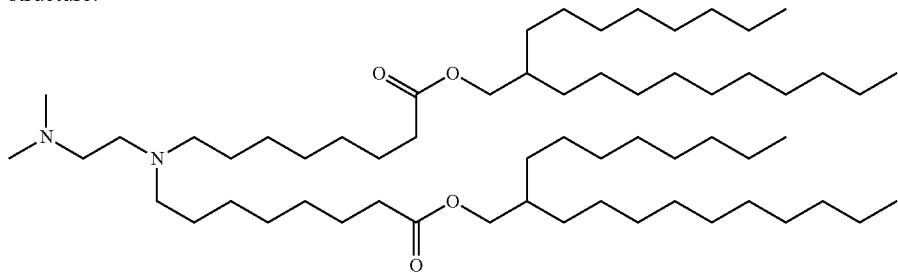

and pharmaceutically acceptable salts thereof. In some embodiments, the compositions and methods of the present invention include a cationic lipid having the compound structure:

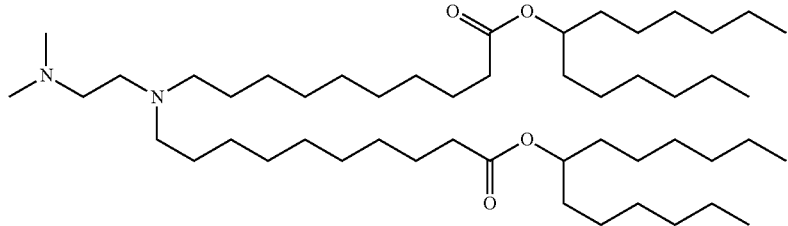 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

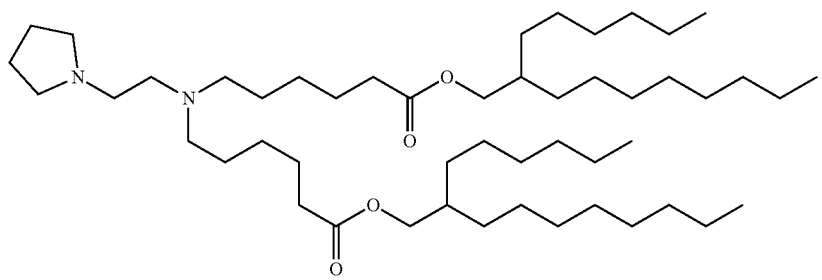 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

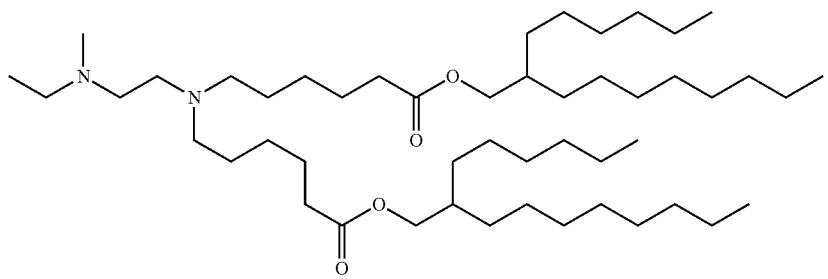 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

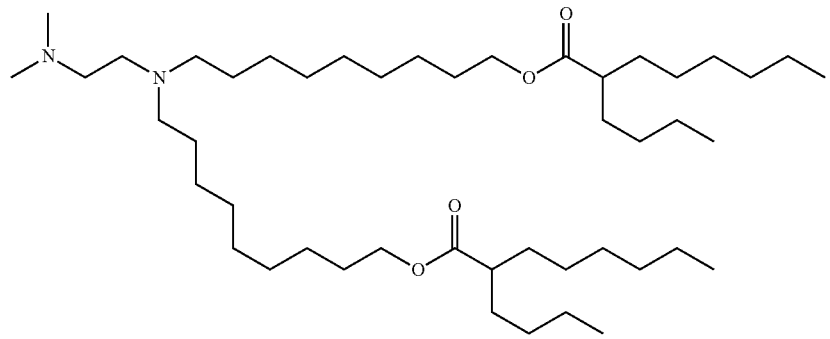 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

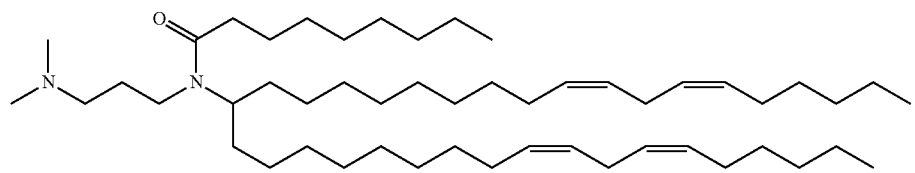 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

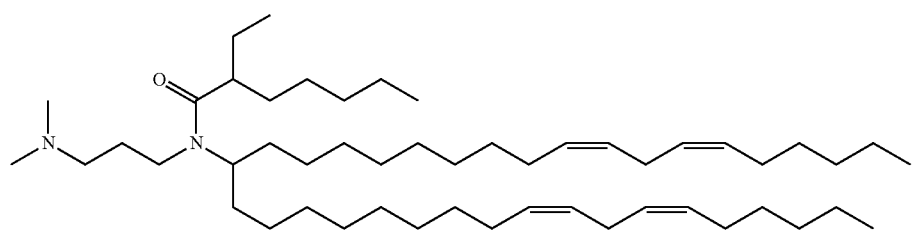 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

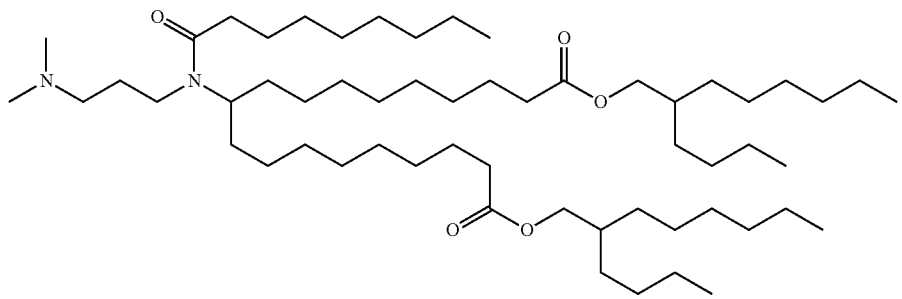 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

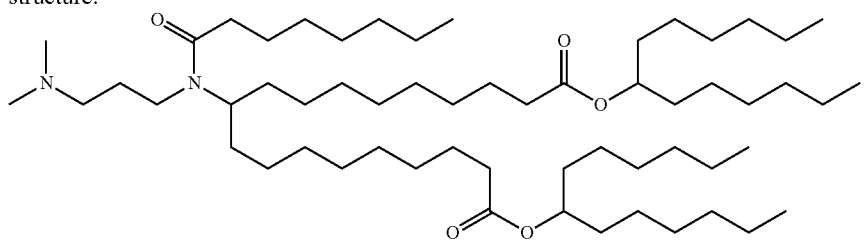

and pharmaceutically acceptable salts thereof. In some embodiments, the compositions and methods of the present invention include a cationic lipid having the compound structure:

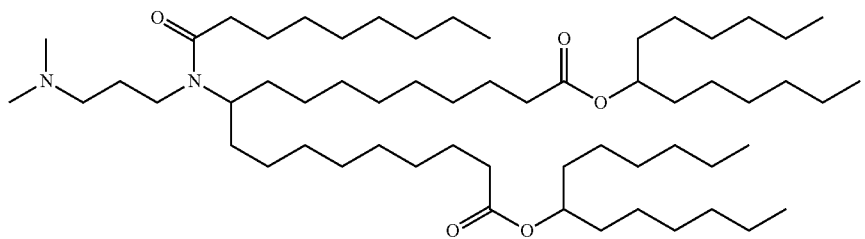 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

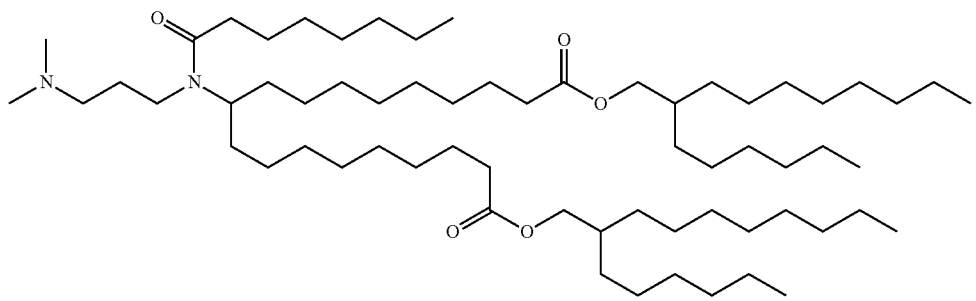 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

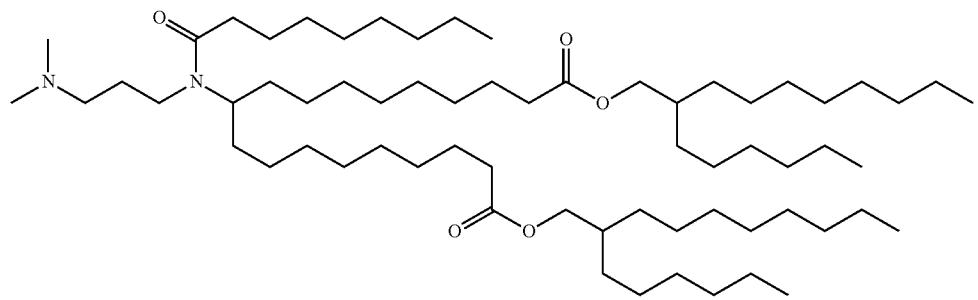 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

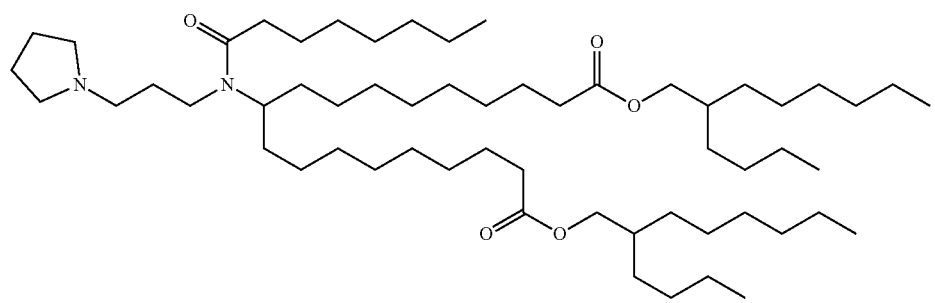 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

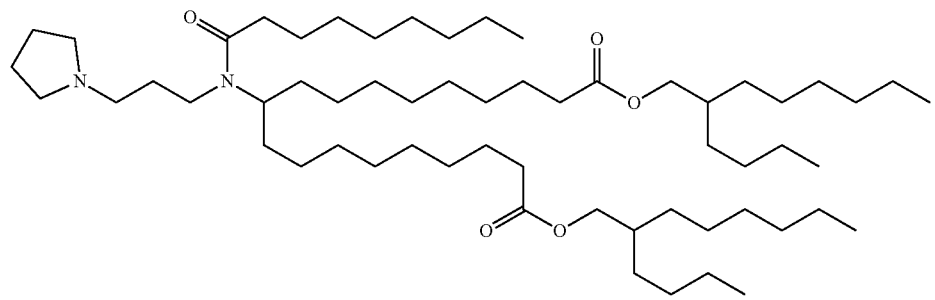 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

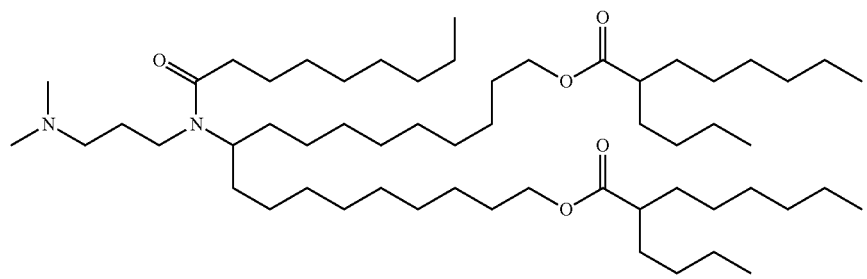 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

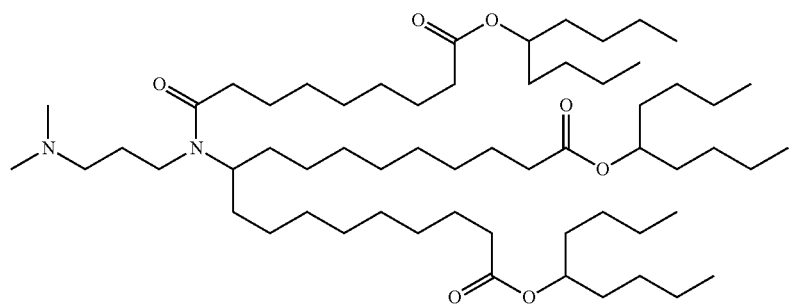 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

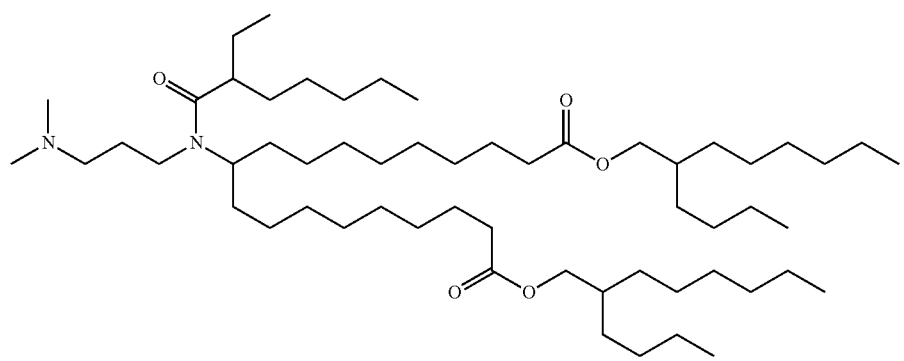 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

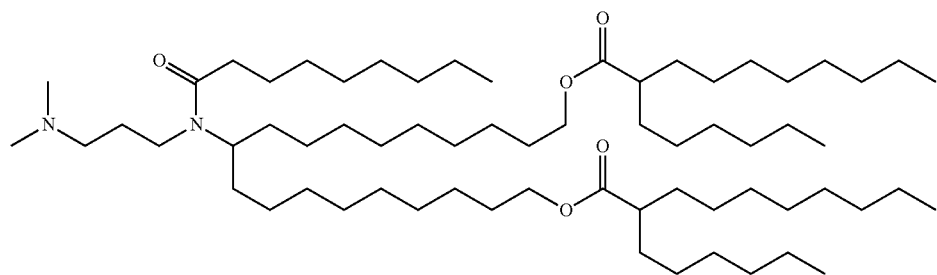 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

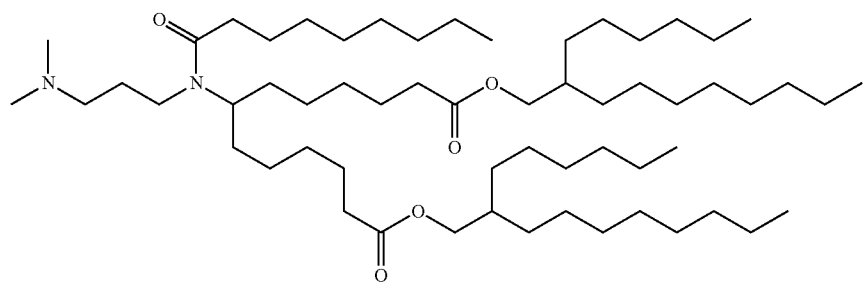 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

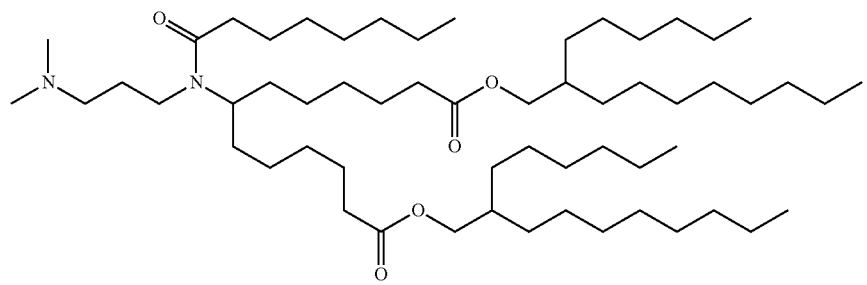 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

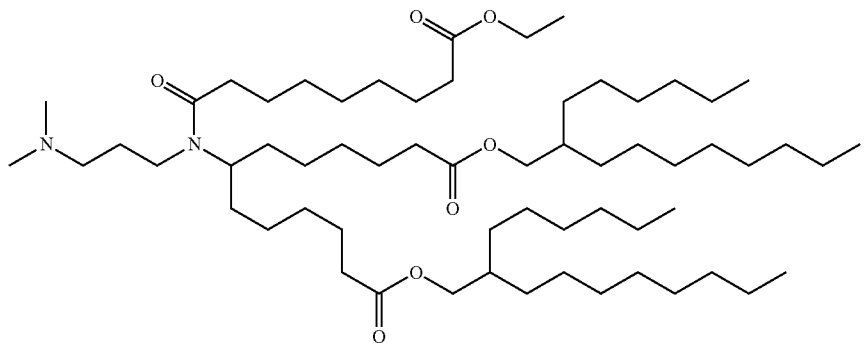 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

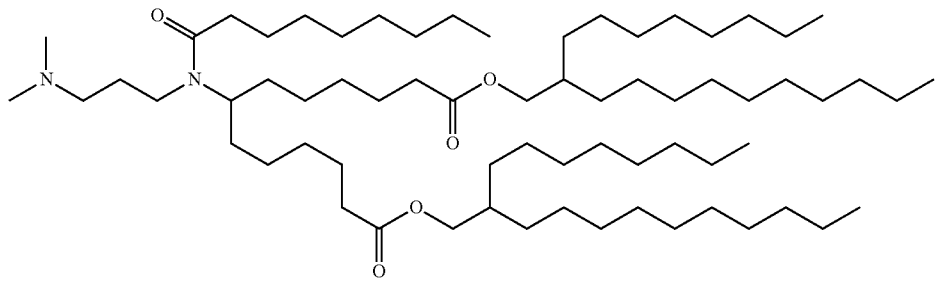 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

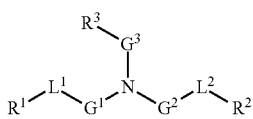

or a pharmaceutically acceptable salt thereof, wherein one of $L^1$ or $L^2$ is —O(C=O)—, —(C=O)O—, —C(=O)—, —O—, —S(O)$_x$, —S—S—, —C(=O)S—, —SC(=O)—, —NR$^a$C(=O)—, —C(=O)NR$^a$—, NR$^a$C(=O)NR$^a$—, —OC(=O)NR$^a$—, or —NR$^a$C(=O)O—; and the other of $L^1$ or $L^2$ is —O(C=O)—, —(C=O)O—, —C(=O)—, —O—, —S(O)$_x$, —S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, OR$^5$, CN, —C(=O)OR$^4$, —OC(=O)R$^4$ or —NR$^5$ C(=O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

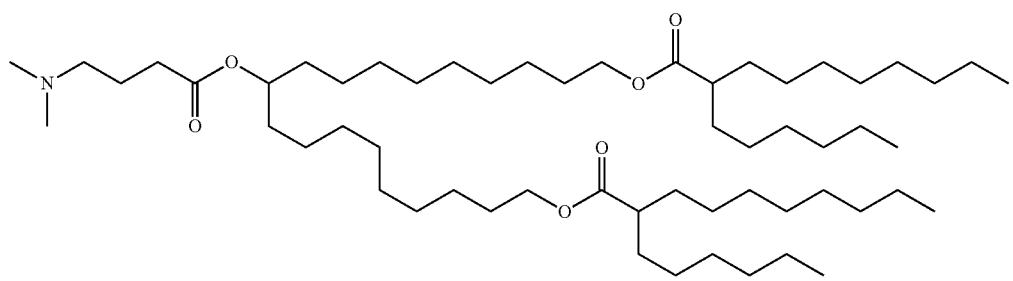 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

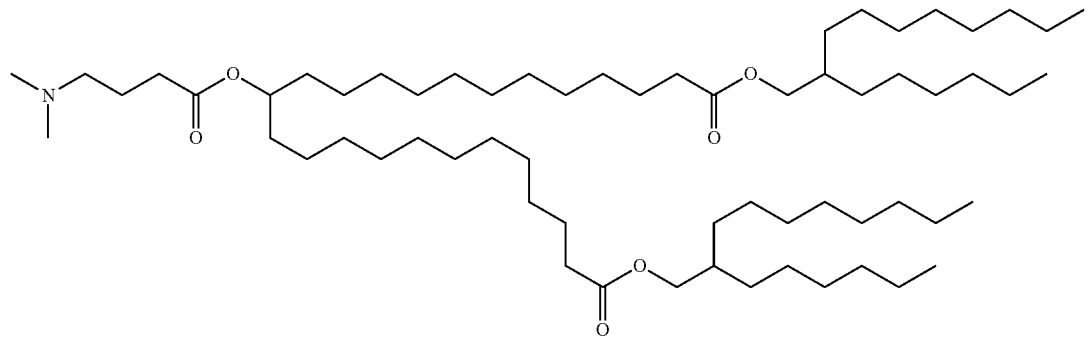 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

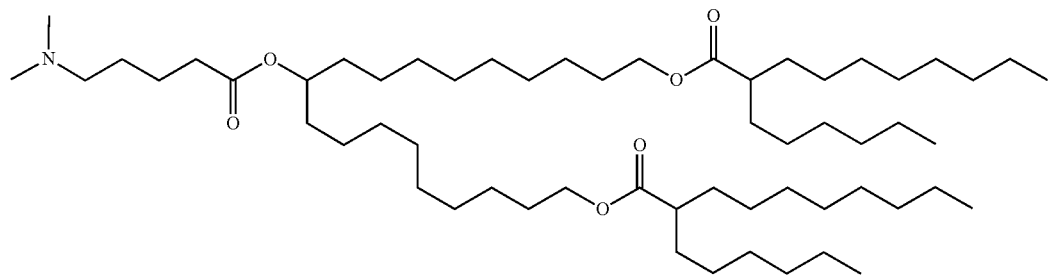 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

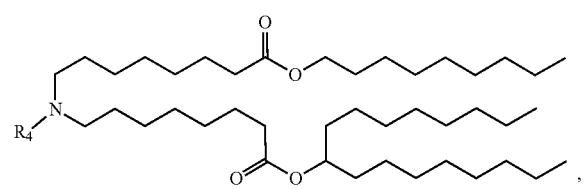

,

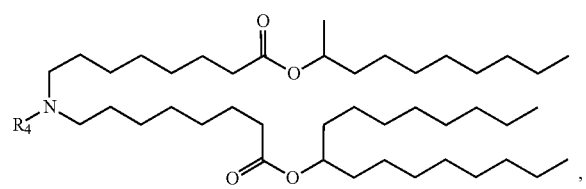

,

-continued

[two additional structures shown]

, and

, and pharmaceutically acceptable salts thereof. For any one of these four formulas, $R_4$ is independently selected from —$(CH_2)_nQ$ and —$(CH_2)_nCHQR$; Q is selected from the group consisting of —OR, —OH, —O(CH$_2$)nN(R)$_2$, —OC(O)R, —CX$_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), and a heterocycle; and n is 1, 2, or 3. In certain embodiments, the compositions and methods of the present invention include a cationic lipid having a compound structure of:

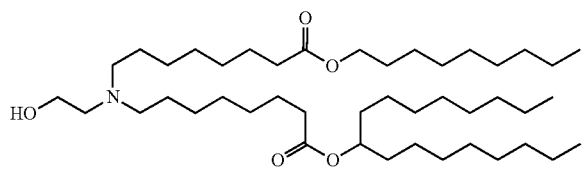 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

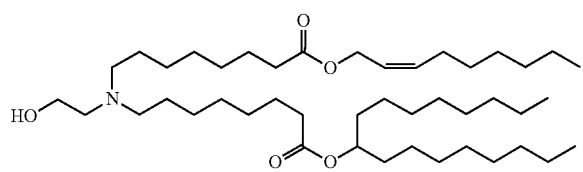 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

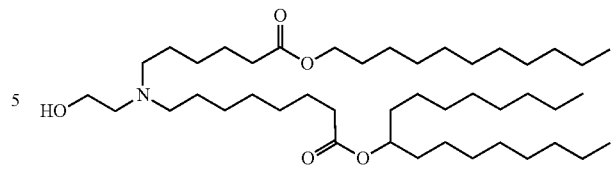

and pharmaceutically acceptable salts thereof. In certain embodiments, the compositions and methods of the present invention include a cationic lipid having a compound structure of:

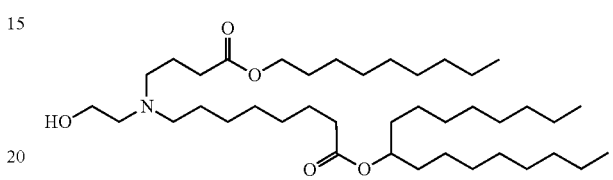

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

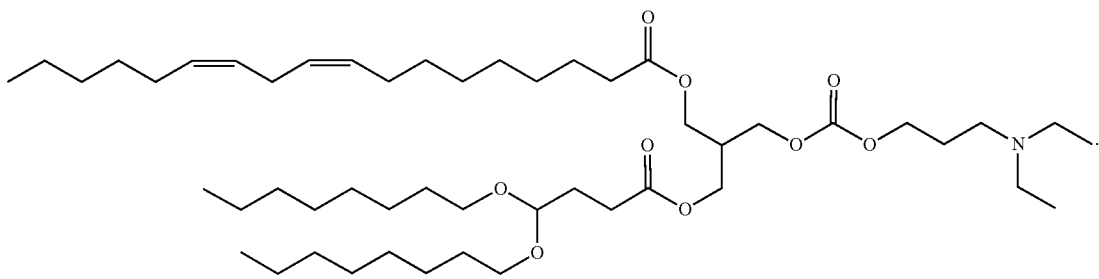 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

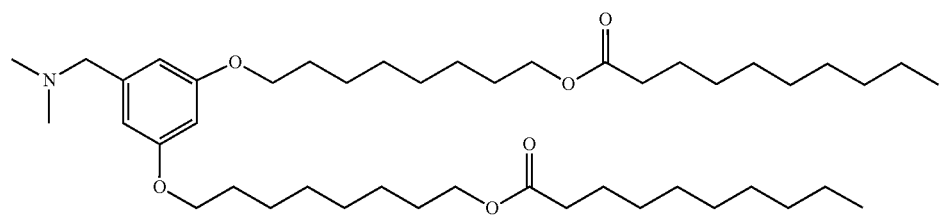 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

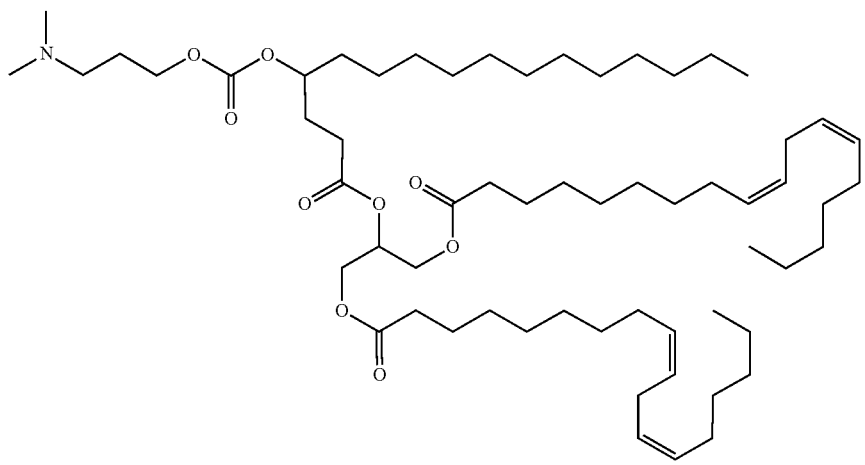 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

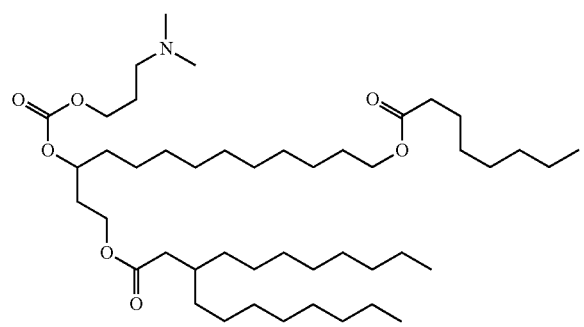 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

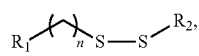

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

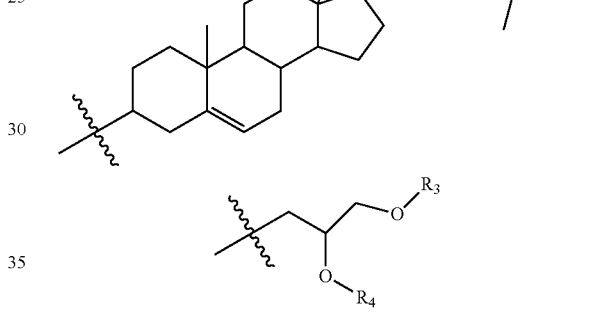

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

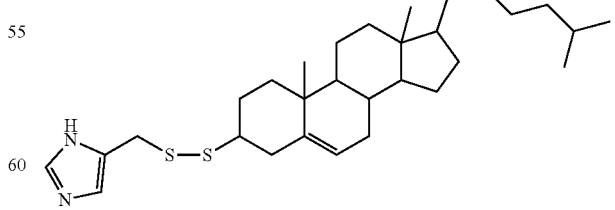

and pharmaceutically acceptable salts thereof. In certain embodiments, the compositions and methods of the present invention include a cationic lipid, "HGT4002", having a compound structure of:

(HGT4002)

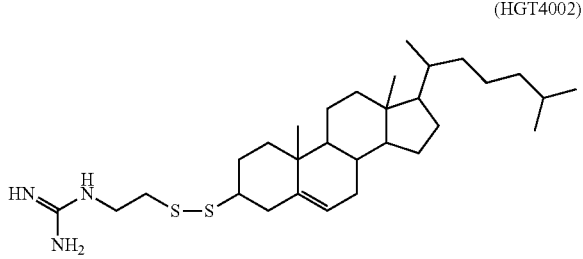 [SMILES: CC(C)CCCC(C)C1CCC2C3CC=C4CC(SSCCNC(=N)N)CCC4(C)C3CCC12C]

and pharmaceutically acceptable salts thereof. In certain embodiments, the compositions and methods of the present invention include a cationic lipid, "HGT4003", having a compound structure of:

(HGT4003)

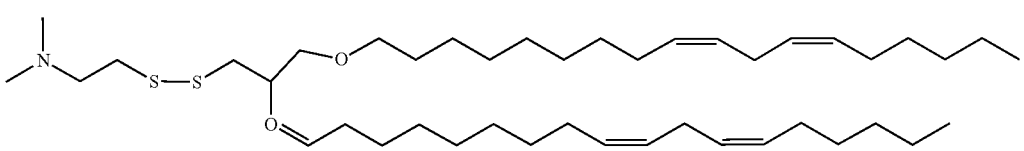

and pharmaceutically acceptable salts thereof. In certain embodiments, the compositions and methods of the present invention include a cationic lipid, "HGT4004", having a compound structure of:

(HGT4004)

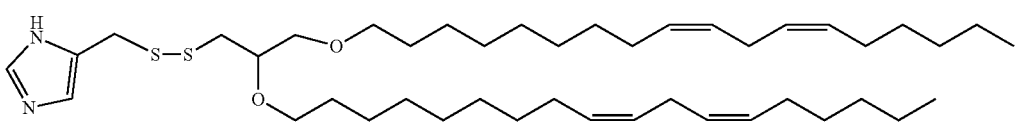

and pharmaceutically acceptable salts thereof. In certain embodiments, the compositions and methods of the present invention include a cationic lipid "HGT4005", having a compound structure of:

(HGT4005)

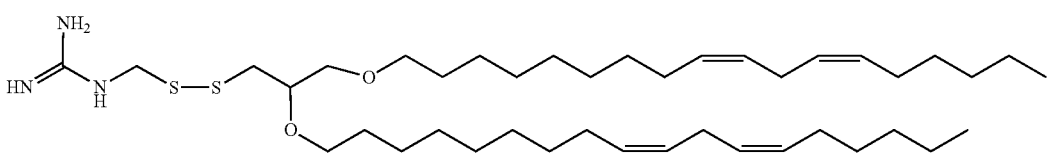

and pharmaceutically acceptable salts thereof.

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethyl-1-(cis,cis-9', 1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoyl-carbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z, 12Z)-octadeca-9,12-dien-1-yloxy]propane-1-amine ("Octyl-CLinDMA"); (2R)-2((8-[(3beta)-cholest-5-en-3-yloxy]octyl)oxy)-N,N-dimethyl-3-[(9Z, 12Z)-octadeca-9,12-dien-1-yloxy]propan-1-amine ("Octyl-CLinDMA (2R)"); (2S)-2-((8-[(3P)-cholest-5-en-3-yloxy]octyl)oxy)-N, fsl-dimethyh3-[(9Z, 12Z)-octadeca-9,12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,12-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)-N,N-dimethyl-2,2-di((9Z,12Z)-octadeca-9,12-dienyl)tetrahydro-3aH-cyclopenta[d][1,3]dioxo1-5-amine ("ALNY-100") and/or 4,7,13-tris(3-oxo-3-(undecylamino)propyl)-N1,N16-diundecyl-4,7,10,13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by the following structure:

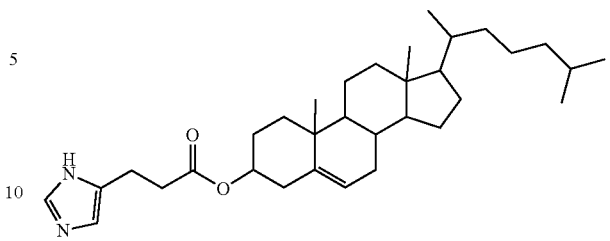

(ICE)

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

Non-Cationic Lipids

In some embodiments, such non-cationic lipids may be used alone, but are preferably used in combination with other lipids, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, a suitable lipid solution includes one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, cholesterol-based lipid(s) constitute(s) at least about 5%, 10%, 20%, 30%, 40%, 50%, 60%, or 70% of the total lipids in a suitable lipid solution by weight or by molar. In some embodiments, cholesterol-based lipid(s) constitute(s) about 30-50% (e.g., about 30-45%, about 30-40%, about 35-50%, about 35-45%, or about 35-40%) of the total lipids in a suitable lipid solution by weight or by molar.

In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5%, greater than 10%, greater than 20%, greater than 30%, or greater than 40%.

The use of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but are not limited to, a polyethylene glycol chain of up to S kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEG-modified lipids and/or polymers described herein at various ratios. As non-limiting examples, a suitable liposome formulation may include a combination selected from cKK-E12, DOPE, cholesterol and DMG-PEG2K; $C_{12}$-200, DOPE, cholesterol and DMG-PEG2K; HGT4003, DOPE, cholesterol and DMG-PEG2K; ICE, DOPE, cholesterol and DMG-PEG2K; or ICE, DOPE, and DMG-PEG2K.

In various embodiments, cationic lipids (e.g., cKK-E12, $C_{12}$-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, $C_{12}$-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5. In some embodiments, the ratio of sterol lipid(s) to non-cationic lipid(s) to PEG-modified lipid(s) is 50:45:5. In some embodiments, the ratio of sterol lipid(s) to non-cationic lipid(s) to PEG-modified lipid(s) is 50:40:10. In some embodiments, the ratio of sterol lipid(s) to non-cationic lipid(s) to PEG-modified lipid(s) is 55:40:5. In some embodiments, the ratio of sterol lipid(s) to non-cationic lipid(s) to PEG-modified lipid(s) is 55:35:10. In some embodiments, the ratio of sterol lipid(s) to non-cationic lipid(s) to PEG-modified lipid(s) is 60:35:5. In some embodiments, the ratio of sterol lipid(s) to non-cationic lipid(s) to PEG-modified lipid(s) is 60:30:10.

In some embodiments, a suitable liposome for the present invention comprises ICE and DOPE at an ICE:DOPE molar ratio of >1:1. In some embodiments, the ICE:DOPE molar ratio is <2.5:1. In some embodiments, the ICE:DOPE molar ratio is between 1:1 and 2.5:1. In some embodiments, the ICE:DOPE molar ratio is approximately 1.5:1. In some embodiments, the ICE:DOPE molar ratio is approximately 1.7:1. In some embodiments, the ICE:DOPE molar ratio is approximately 2:1. In some embodiments, a suitable liposome for the present invention comprises ICE and DMG-PEG-2K at an ICE:DMG-PEG-2K molar ratio of >10:1. In some embodiments, the ICE:DMG-PEG-2K molar ratio is <16:1. In some embodiments, the ICE:DMG-PEG-2K molar ratio is approximately 12:1. In some embodiments, the ICE:DMG-PEG-2K molar ratio is approximately 14:1. In some embodiments, a suitable liposome for the present invention comprises DOPE and DMG-PEG-2K at a DOPE:DMG-PEG-2K molar ratio of >5:1. In some embodiments, the DOPE: DMG-PEG-2K molar ratio is <11:1. In some embodiments, the DOPE: DMG-PEG-2K molar ratio is approximately 7:1. In some embodiments, the DOPE: DMG-PEG-2K molar ratio is approximately 10:1. In some embodiments, a suitable liposome for the present invention comprises ICE, DOPE and DMG-PEG-2K at an ICE:DOPE:DMG-PEG-2K molar ratio of 50:45:5. In some embodiments, a suitable liposome for the present invention comprises ICE, DOPE and DMG-PEG-2K at an ICE:DOPE:DMG-PEG-2K molar ratio of 50:40:10. In some embodiments, a suitable liposome for the present invention comprises ICE, DOPE and DMG-PEG-2K at an ICE:DOPE: DMG-PEG-2K molar ratio of 55:40:5. In some embodiments, a suitable liposome for the present invention comprises ICE, DOPE and DMG-PEG-2K at an ICE:DOPE: DMG-PEG-2K molar ratio of 55:35:10. In some embodiments, a suitable liposome for the present invention comprises ICE, DOPE and DMG-PEG-2K at an ICE:DOPE: DMG-PEG-2K molar ratio of 60:35:5. In some embodiments, a suitable liposome for the present invention comprises ICE, DOPE and DMG-PEG-2K at an ICE:DOPE: DMG-PEG-2K molar ratio of 60:30:10.

The liposomal transfer vehicles for use in the compositions of the invention can be prepared by various techniques which are presently known in the art. Various methods are described in published U.S. Application No. US 2011/0244026, published U.S. Application No. US 2016/0038432 and provisional U.S. Application No. 62/580,155, filed Nov. 1, 2017 and can be used to practice the present invention, all of which are incorporated herein by reference.

The following applications including lipid compositions filed by the Applicant are hereby fully incorporated by reference: 62/672,194 filed May 16, 2018; 62/676,147, filed May 24, 2018; and applications to be filed on even date with the present application, titled, Cationic Lipids Comprising a Steroidal Moiety; titled, Phosphoester Cationic Lipids; titled, Macrocyclic Lipids; titled, Vitamin K Cationic Lipids; titled, Vitalipids II; titled, Vitalipids III; titled, Vitalipids IV.

mRNA-Loaded Nanoparticles

Any desired lipids may be mixed at any ratios suitable for encapsulating mRNAs. In some embodiments, a suitable lipid solution contains a mixture of desired lipids including cationic lipids, non-cationic lipids, cholesterol and/or PEGylated lipids.

In some embodiments, a process for encapsulating mRNA in lipid nanoparticles comprises mixing an mRNA solution and a lipid solution, wherein the mRNA solution and/or the lipid solution are heated to a pre-determined temperature greater than ambient temperature prior to mixing to form lipid nanoparticles that encapsulate mRNA (see U.S. patent application Ser. No. 14/790,562 entitled "Encapsulation of messenger RNA", filed Jul. 2, 2015 and its provisional U.S. patent application Ser. No. 62/020,163, filed Jul. 2, 2014, the disclosure of which are hereby incorporated in their entirety).

In some embodiments, a process for encapsulating mRNA in lipid nanoparticles comprises combining pre-formed lipid nanoparticles with mRNA (see U.S. Provisional Application Ser. No. 62/420,413, filed Nov. 10, 2016 and U.S. Provisional Application Ser. No. 62/580,155, filed Nov. 1, 2017, the disclosures of which are hereby incorporated by reference). In some embodiments, combining pre-formed lipid nanoparticles with mRNA results in lipid nanoparticles that show improved efficacy of intracellular delivery of the mRNA. In some embodiments, combining pre-formed lipid nanoparticles with mRNA results in very high encapsulation efficiencies of mRNA encapsulated in lipid nanoparticles (i.e., in the range of 90-95%). In some embodiments, combining pre-formed lipid nanoparticles with mRNA is achieved with pump systems which maintain the lipid/mRNA (N/P) ratio constant throughout the process and which also afford facile scale-up.

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

In some embodiments a method of preparing a lipid nanoparticle containing mRNA has been identified, which involves combining pre-formed lipid nanoparticles with mRNA under conditions which, due to the order of addition of such components, the resultant formulated particles show improved potency and efficacy. The mixing of the components is achieved with pump systems which maintain the lipid/mRNA (N/P) ratio constant throughout the process and which also afford facile scale-up. This process is described in detail in the Applicant's international application, PCT/US17/61113, filed on Nov. 10, 2017, and US application filed on even date having U.S. Ser. No. 15/809,680, claiming priority to application No. 62/420,413 filed Nov. 10, 2016, all of which are fully incorporated herein by reference. The above indicated process of formulation is often referred herein as "Remix" formulation.

Vaccine Compositions

Immunogenic compositions of the invention can contain additional substances, such as adjuvants to enhance the effectiveness of the vaccines, and pharmaceutically acceptable carriers including, but not limited to, wetting or emulsifying agents, or buffering agents (Remington's Pharmaceutical Sciences, 18th edition, Mack Publishing Company, (ed.) 1980).

Adjuvants

Suitable adjuvants may include, but are not limited to, mineral salts (e.g., $AlK(SO_4)_2$, $AlNa(SO_4)_2$, $AlNH(SO_4)_2$, silica, aluminum, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8); the CCR5 inhibitor CMPD167 (see Veazey, R. S. et al (2003) J. Exp. Med. 198: 1551-1562); and Squalene emulsion, i.e., MF59.

In some embodiments, the adjuvant is another RNA.

Adjuvant widely used in humans has been aluminum. In some embodiments, a suitable adjuvant is aluminum phosphate. In some embodiments, a suitable adjuvant is aluminum hydroxide. In some embodiments, a suitable adjuvant is a combination of aluminum phosphate and aluminum hydroxide. Saponin and its purified component Quil A, Freund's complete adjuvant and other adjuvants are typically used in research and veterinary applications; however, new chemically defined preparations such as muramyl dipeptide, monophosphoryl lipid A, phospholipid conjugates such as those described by Goodman-Snitkoff et al. J. Immunol. 147:410-415 (1991) and incorporated by reference herein.

Carriers, Excipients

To facilitate expression of mRNA in vivo, delivery vehicles such as lipid nanoparticles, including liposomes, can be formulated in combination with one or more additional nucleic acids, carriers, targeting ligands or stabilizing reagents, or in pharmacological compositions where it is mixed with suitable excipients. In some embodiments, the lipid nanoparticles encapsulating mRNA are simultaneously administrated with hyaluronidase. Techniques for formulation and administration of drugs may be found in "Remington's Pharmaceutical Sciences," Mack Publishing Co., Easton, Pa., latest edition.

Typically, immunogenic vaccine compositions according to the present invention include a pharmaceutically acceptable carrier. In general, pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like.

Pharmaceutically acceptable carriers are determined in part by the particular composition being administered, as well as by the particular method used to administer the composition. Accordingly, there is a wide variety of suitable formulations of immunogenic compositions of the present invention. In some embodiment, an immunogenic vaccine composition is formulated for parenteral (i.e., intramuscular, intradermal or subcutaneous) administration or nasopharyngeal (i.e., intranasal) administration. Typically, formulations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the immunogenic compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Alternatively or additionally, liposomally encapsulated mRNAs and compositions of the invention may be administered in a local rather than systemic manner.

Administration can be accomplished by single or multiple doses.

Provided methods of the present invention contemplate single as well as multiple administrations of a therapeutically effective amount of the vaccination agents (e.g., mRNA encoding an antigen) described herein. Vaccination agents can be administered at regular intervals, depending on the nature, severity and extent of the subject's condition, such as stage of infection, prevalance demographics, or stage of cancer. In some embodiments, a therapeutically effective amount of the vaccination agent (e.g., mRNA encoding an antigen) of the present invention may be administered periodically at regular intervals (e.g., once every year, once every six months, once every five months, once every three months, bimonthly (once every two months), monthly (once every month), biweekly (once every two weeks), twice a month, once every 30 days, once every 28 days, once every 14 days, once every 10 days, once every 7 days, weekly, twice a week, daily or continuously.

In some embodiments, provided liposomes and/or compositions are formulated such that they are suitable for extended-release of the mRNA contained therein. Such extended-release compositions may be conveniently administered to a subject at extended dosing intervals. For example, in some embodiments, the compositions of the present invention are administered to a subject twice a day, daily or every other day. In a preferred embodiment, the compositions of the present invention are administered to a subject twice a week, once a week, once every 7 days, once every 10 days, once every 14 days, once every 28 days, once every 30 days, once every two weeks, once every three weeks, or more preferably once every four weeks, once a month, twice a month, once every six weeks, once every eight weeks, once every other month, once every three months, once every four months, once every six months, once every eight months, once every nine months or annually. Also contemplated are compositions and liposomes which are formulated for depot administration (e.g., intramuscularly, subcutaneously, intravitreally) to either deliver or release mRNA over extended periods of time. Preferably, the extended-release means employed are combined with modifications made to the mRNA to enhance stability.

As used herein, the term "therapeutically effective amount" is largely based on the total amount of the vaccinating agent contained in the vaccine compositions of the present invention. Generally, a therapeutically effective amount is sufficient to achieve a meaningful benefit to the subject (e.g., treating, modulating, curing, preventing and/or ameliorating an infection or cancer). For example, a therapeutically effective amount may be an amount sufficient to achieve a desired therapeutic and/or prophylactic effect. Generally, the amount of a therapeutic agent (e.g., mRNA encoding an antigen) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

In some embodiments, a priming dose of the vaccine is administered on week 0, followed by one or more additional vaccine doses. In some embodiments an additional one, two or three vaccine doses, also known as booster doses are administered after the priming dose. In some embodiments, the priming dose and booster dose(s) have specific time intervals. In some embodiments, the priming dose and the booster dose is administered one week apart, or two weeks apart, or any other interval suitable for the vaccine and the desired immunological response. In some embodiments, the time interval between two consecutive booster dose is same as the interval between the priming and the booster dose. In some embodiments the time interval between two consecutive booster doses is different from the time interval between the priming and the booster dose.

A therapeutically effective amount is commonly administered in a dosing regimen that may comprise multiple unit doses. For any particular vaccine, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific vaccine agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

In some embodiments, the therapeutically effective dose ranges from about 0.005 mg/kg to 500 mg/kg body weight, e.g., from about 0.005 mg/kg to 400 mg/kg body weight, from about 0.005 mg/kg to 300 mg/kg body weight, from about 0.005 mg/kg to 200 mg/kg body weight, from about 0.005 mg/kg to 100 mg/kg body weight, from about 0.005 mg/kg to 90 mg/kg body weight, from about 0.005 mg/kg to 80 mg/kg body weight, from about 0.005 mg/kg to 70 mg/kg body weight, from about 0.005 mg/kg to 60 mg/kg body weight, from about 0.005 mg/kg to 50 mg/kg body weight, from about 0.005 mg/kg to 40 mg/kg body weight, from about 0.005 mg/kg to 30 mg/kg body weight, from about 0.005 mg/kg to 25 mg/kg body weight, from about 0.005 mg/kg to 20 mg/kg body weight, from about 0.005 mg/kg to 15 mg/kg body weight, from about 0.005 mg/kg to 10 mg/kg body weight.

In some embodiments, the therapeutically effective dose of the vaccine is greater than about 0.1 mg/kg body weight, greater than about 0.5 mg/kg body weight, greater than about 1.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight. In a particular embodiment, the therapeutically effective dose is 1.0 mg/kg body weight. In some embodiments, the therapeutically effective dose of 1.0 mg/kg body weight is administered subcutaneously, intramuscularly or intravenously.

In some embodiments, about 0.3 µg of vaccine is administered per dose. In some embodiments, about 0.4 µg of vaccine is administered. In some embodiments, about 0.5 µg of vaccine is administered. In some embodiments, about 0.6 µg of vaccine is administered. In some embodiments, about 0.7 µg of vaccine is administered. In some embodiments, about 0.8 µg of vaccine is administered. In some embodiments, about 0.9 µg of vaccine is administered. In some embodiments, about 1 µg of vaccine is administered. In some embodiments, about 2 µg of vaccine is administered. In some embodiments, about 3 µg of vaccine is administered. In some embodiments, about 4 µg of vaccine is administered. In some embodiments, about 5 µg of vaccine is administered. In some embodiments, about 6 µg of vaccine is administered. In some embodiments, about 7 µg of vaccine is administered. In some embodiments, about 8 µg of vaccine is administered. In some embodiments, about 9 µg of vaccine is administered. In some embodiments, about 10 µg of vaccine is administered. In some embodiments, about 12, 15, 20, 30, 50 or 100 µg of vaccine, or any amount in between, is administered. In some embodiments, upto about 1 mg vaccine is administered per dose. In some embodiments, upto about 10 mg of vaccine is administered per dose. In some embodiments, upto about 100 mg of vaccine is administered per dose.

In some embodiments, the priming dose and the subsequent vaccine dose or doses are same in amount. In some embodiments, the priming dose and the subsequent vaccine dose or doses are different in amount.

In some embodiments, the administration of the composition results in expression of the antigen encoded by mRNA in the lymph nodes of the subject. In some embodiments, the administration of the composition results in expression of the antigen encoded by mRNA in the lymphocytes of the subject.

In some embodiments, the administration of the composition results in an antigen specific antibody response. In some embodiments, the antigen specific antibody response is measured by the presence of antigen-specific antibodies in serum.

In some embodiments, the administration of the composition results in an antigen specific T-cell response. In some embodiments, the antigen specific T-cell response is measured by cytokine response. In some embodiments, the antigen specific T-cell response is measured by IFN-$\gamma$ ELISPOT in splenocytes.

In some embodiments, the antigen specific antibody response and/or the antigen specific T-cell response is detectable at least 24 hours, 2 days, 3 days, 4 days, 5 days, 6 days, 1 week, 2 weeks, 3 weeks, 4 weeks, or 1 month post-administration.

Also contemplated herein are lyophilized pharmaceutical compositions comprising one or more of the liposomes disclosed herein and related methods for the use of such compositions as disclosed for example, in International Patent Application PCT/US12/41663, filed Jun. 8, 2012, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the provided liposomes and compositions comprising mRNA are delivered subcutaneously and the mRNA is expressed in a cell or tissue type other than the subcutis. Certain compositions result in delivery and expression bias in a certain tissue other than the site of administration. The present invention provides compositions for subcutaneous administration that result in robust expression in lymph nodes. Other exemplary tissues in which delivered mRNA may be expressed include, but are not limited to, the liver, kidney, heart, spleen, serum, brain, skeletal muscle, lymph nodes, skin, and/or cerebrospinal fluid.

In some embodiments, administering a provided composition results in increased expression of the mRNA administered, and/or increased expression and activity level of other enzymes or proteins in a biological sample from a subject as compared to a baseline expression or activity level before treatment or administration. In some embodiments, administering a provided composition results in increased cytokine expression or chemokine expression compared to a baseline expression or activity level before treatment. For example, a T cell vaccine stimulating and activating a cytotoxic T cell would result in increased IFN-gamma production over baseline level. IFN-$\gamma$ and other cytokines and chemokines are well known in the art as immune response or activation markers. Typically, the baseline level is measured immediately before treatment. Biological samples include, for example, whole blood, serum, plasma, urine and tissue samples (e.g., muscle, liver, skin fibroblasts). In some embodiments, administering a provided composition results in increased expression or activity of an immune response marker level by at least about 10%, 20%, 30%, 40%, 50%, 60%, 70%, 80%, 90%, or 95% as compared to the baseline level immediately before treatment. In some embodiments, administering a provided composition results in increased mRNA expression or activity level in a biological sample from a subject as compared to subjects who were not treated. In some embodiments, administering a provided composition results in increased expression or activity level of a therapeutic protein in a biological sample from a subject as compared to subjects who were not treated.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, 96 hours, 1 week, 2 weeks, or 1 month after administration of provided liposomes and/or compositions.

In some embodiments, a therapeutically effective dose of the provided composition, when administered.

EXAMPLES

While certain compounds, compositions and methods of the present invention have been described with specificity in accordance with certain embodiments, the following examples serve only to illustrate the compounds of the invention and are not intended to limit the same.

Lipid Materials

The formulations described in the following Examples, unless otherwise specified, contain a multi-component lipid mixture of varying ratios employing one or more cationic lipids, helper lipids (e.g., non-cationic lipids and/or cholesterol lipids) and PEGylated lipids designed to encapsulate various nucleic acid materials. Cationic lipids for the process can include, but are not limited to, cKK-E12 (3,6-bis (4-(bis(2-hydroxydodecyl)amino)butyl)piperazine-2,5-dione), OF-02, Target 23, Target 24, Imidazole cholesterol ester (ICE), HGT5000, HGT5001, HGT4003, DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869), dialkylamino-based, imidazole-based, guanidinium-based, etc. Helper lipids can include, but are not limited, to DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), DOPC (1,2-dioleyl-sn-glycero-3-phosphotidylcholine), cholesterol, etc. PEGylated lipids can include, but are not limited to, a poly(ethylene) glycol chain of up to 5 kDa in length covalently attached to a lipid with alkyl chain(s) of $C_6$-$C_{20}$ length.

mRNA Materials

In some embodiments, codon-optimized messenger RNA encoding target protein was synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A). 5' and 3' untranslated regions present in each mRNA product are represented as X and Y, respectively and defined as stated previously.

Example 1

A Single Dose Efficacy Comparison of Different Lipid Formulations for Expression of mRNA in Serum Using human erythropoietin (hEPO) as a sensitive quantitative measure of mRNA transfection efficacy, three different lipid formulations ML-2, ML-7 and MC3 were compared for expression levels of hEPO protein in the serum. MC3 is understood to be the state of the art formulation for certain RNA delivery platforms. Mice received intravenous administrations of either 0.3 mg/Kg or 1 mg/Kg of mRNA in lipid formulations comprising either ML-2, or ML-7 or MC3. hEPO protein levels were measured in the serum at 6 and 24 hours post administration respectively.

As shown in FIGS. 1A and 1B, both ML-2 and ML-7 yielded higher levels of serum hEPO levels irrespective of the dose, measured at 6 and 24 hours respectively. These results show that the lipid formulations ML-2 and ML-7 are more efficient at mRNA delivery and expression than the conventional MC3 formulation.

Example 2

Figure 2:
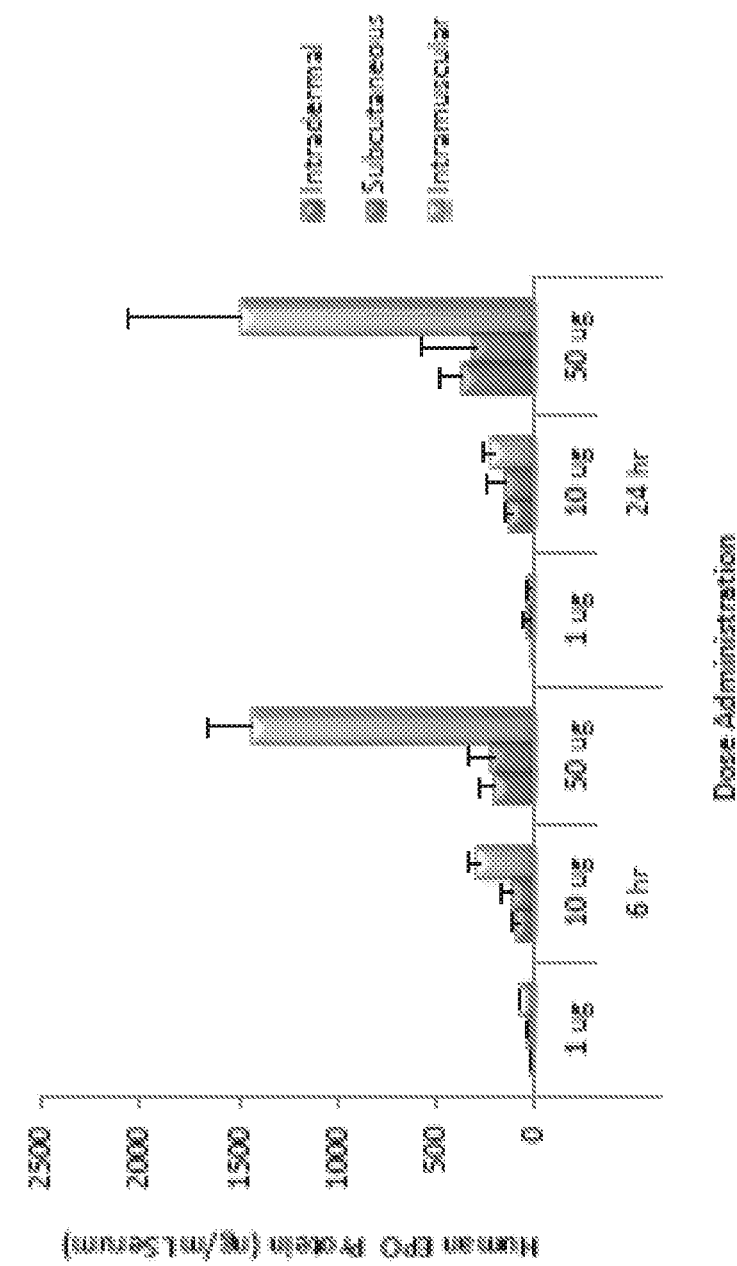
FIG. 2 depicts comparison data on efficacy of three different routes of in vivo human erythropoietin (hEPO) mRNA delivery, as indicated by measuring hEPO protein in the serum.

A Single Dose Efficacy Comparison of Routes of mRNA Delivery for Detection of Expressed Protein in Serum In this exemplary experiment, intradermal, subcutaneous and intramuscular routes of hEPO mRNA administration were compared for hEPO protein expression in the serum. Mice were administered either 1, 10 or 50 µg of hEPO mRNA either subcutaneously, or intradermally or intramuscularly. Serum hEPO protein levels were measured in the serum at 6 and 24 hours post administration. As shown in FIG. 2, intramuscular administration results in the highest for serum expression of the delivered mRNA among the three routes of administration studied at 6 and 24 hours.

Example 3

Robust mRNA Expression in Lymph Nodes Resulting from Subcutaneous and Intradermal Delivery of mRNA In this exemplary study, a single dose comparison of delivery routes, subcutaneous, intradermal and intramuscular were performed on mice using Firefly Luciferase (FFL) as the experimental mRNA. Male CD1 mice (N=13), 6-8 weeks of age, were administered 1 mg/Kg FFL mRNA either subcutaneously (SC), or intradermally (ID), or intramuscularly (IM), at a concentration of 0.2 mg/mL and a dose volume of 5 mL/Kg, or an adequate no mRNA control. At 24 hours post administration, all animals were dosed with luciferin 150 mg/Kg (60 mg/mL) via intraperitoneal injection at 2.5 mL/Kg. All mice were euthanized 15 minutes after luciferin administration and whole body intracardiac perfusion was performed with saline. Liver, spleen, heart, lungs, kidneys, and brachial, axillary and inguinal lymph nodes were collected and prepared for in vivo luciferase assay by imaging using IVIS Lumina equipment and protocol. As shown below, the results indicate that the route of administration affects delivery and expression of an mRNA in vivo.

Figure 3:
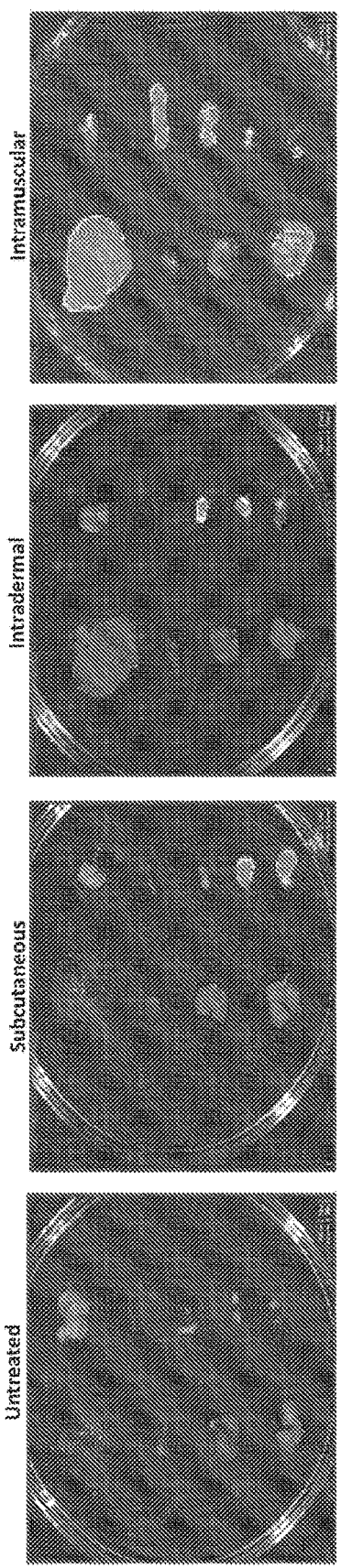
FIG. 3 depicts images of FFL expression in different mouse tissues, showing comparison of delivery routes on tissue specific enrichment of FFL expression.
Figure 3:
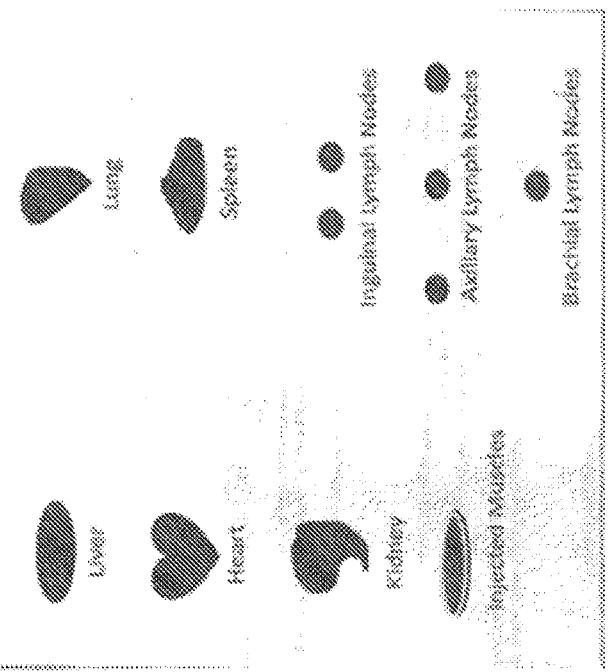

Table 1 shows the results expressed as average total fluorescence in each treatment group, in the various tissues as indicated. Enrichment FFL mRNA in lymph nodes was noticed in all routes of delivery. However, surprisingly, delivery by subcutaneous and intradermal routes led to robust FFL protein expression in the axillary and brachial lymph nodes, as compared to liver and spleen, whereas intramuscular delivery led to preferential expression in the liver, spleen, muscles and inguinal lymph nodes, with moderate expression in the axillary and brachial lymph nodes. FIG. 3 shows fluorescence images of tissues from a representative mouse in each group. (Groups: no mRNA control, subcutaneous administration, intradermal administration, and intramuscular administration). A diagram indicating the placement of various tissues on a petri dish is provided as index in the figure for identification of the different tissues by shape and position.

TABLE 1

| Tissue | Average total flux (p/s) | Std. dev. |
|---|---|---|
| Subcutaneous | | |
| Liver | 6,388,250 | 5.78E+06 |
| Heart | 124,280 | 5.44E+04 |
| Kidneys | 372,150 | 9.61E+04 |
| Muscles | 672,725 | 1.89E+05 |
| Lungs | 77,075 | 1.35E+04 |
| Spleen | 337,175 | 2.45E+05 |
| Inguinal LN | 759,325 | 1.24E+05 |
| Axillary LN | 27,222,500 | 6.18E+06 |
| Brachial LN | 19,202,500 | 1.04E+07 |
| Intradermal | | |
| Liver | 41,160,000 | 4.17E+07 |
| Heart | 113,060 | 4.96E+04 |
| Kidneys | 149,208 | 7.11E+04 |
| Muscles | 804,900 | 5.92E+05 |
| Lungs | 170,458 | 1.38E+05 |
| Spleen | 1,762,200 | 8.36E+05 |
| Inguinal LN | 10,862,250 | 4.84E+06 |
| Axillary LN | 18,867,500 | 4.46E+06 |
| Brachial LN | 3,201,000 | 9.57E+05 |
| Intramuscular | | |
| Liver | 133,300,000 | 2.66E+06 |
| Heart | 1,183,925 | 3.38E+05 |
| Kidneys | 4,788,750 | 1.29E+06 |
| Muscles | 75,980,000 | 8.66E+06 |
| Lungs | 2,365,750 | 4.16E+05 |
| Spleen | 39,500,000 | 3.98E+06 |
| Inguinal LN | 30,160,000 | 4.28E+06 |
| Axillary LN | 4,383,200 | 2.94E+06 |
| Brachial LN | 6,823,750 | 3.20E+06 |

Example 4

Evaluating Bio-Distribution of FFL LNP Using Different Cationic Lipids

Figure 4:
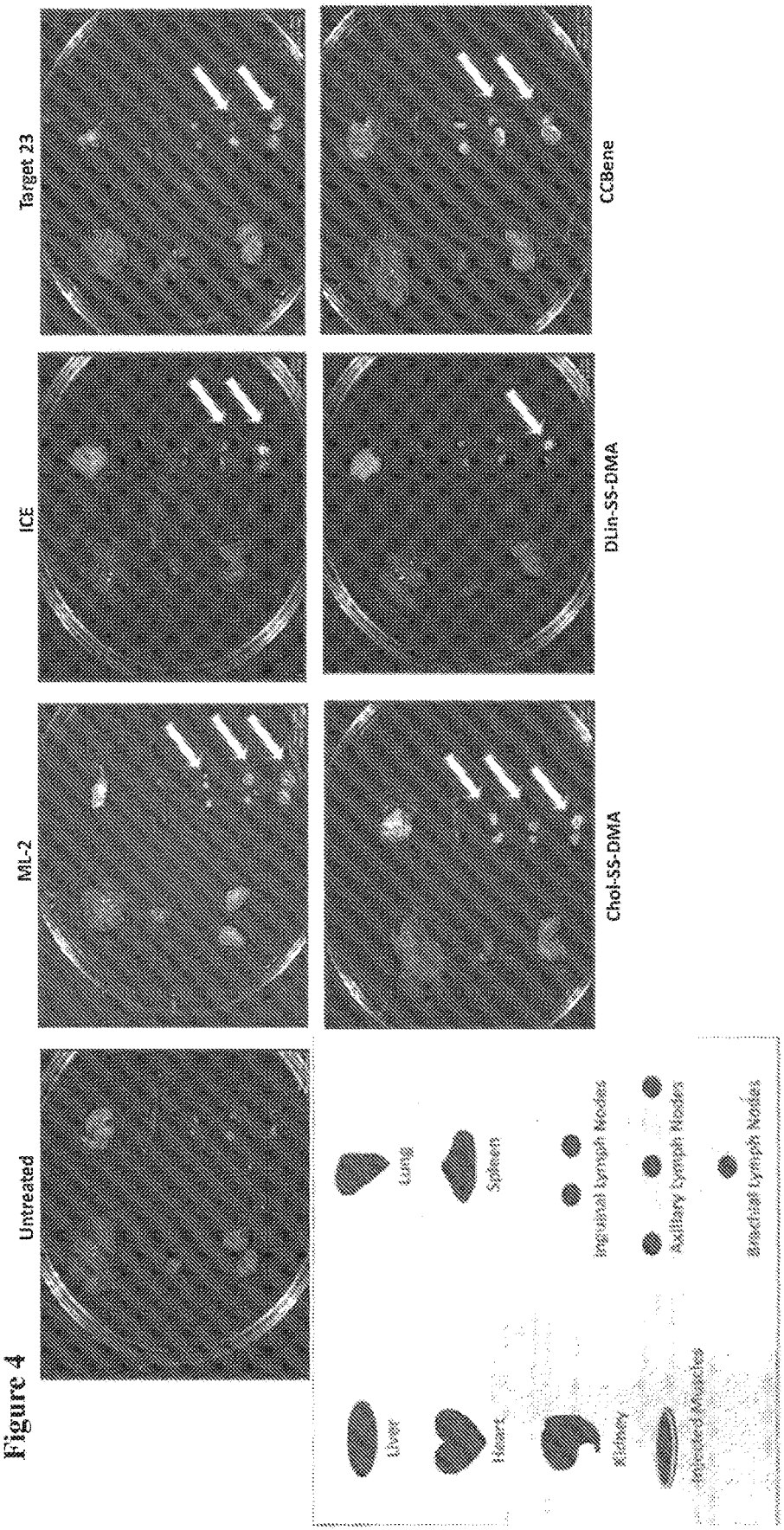
FIG. 4 depicts images of FFL expression in different mouse tissues, showing comparison of different cationic lipids on tissue specific enrichment of FFL expression.

In this example, mice were administered a single subcutaneous injection of FFL-LNP (1 mg/Kg) using the protocol as described in the study under Example 3, but using different cationic lipid components in the LNP composition. Results indicate that multiple formulations lead to enrichment of the mRNA and robust expression in the lymph nodes. However, use of certain cationic lipids led to biased expression of the mRNA in the lymph nodes, for example, compositions comprising ICE (LNP composition 2 in Table 2), Target 23 (LNP compositions 4 and 5 in Table 2), ML2 (LNP composition 1 in Table 2), and CCBene (LNP composition 8 in Table 2) lead to robust expression of FFL mRNA in the lymph nodes. Representative tissue images are shown in FIG. 4. Tissues with high fluorescence are indicated by an arrow. A diagram indicating the placement of various tissues on a petri dish is provided as index in the figure for identification of the different tissues by shape and position. Table 2 provides the average fluorescence in various tissues resulting from FFL expression.

TABLE 2

| Tissue | Ave | SD |
|---|---|---|
| No RNA control | | |
| Liver | 19,573 | 6.38E+03 |
| Heart | 8,139 | 1.34E+03 |
| Kidneys | 9,499 | 2.26E+03 |
| Lungs | 13,898 | 9.34E+02 |
| Spleen | 10,800 | 2.27E+03 |
| Inguinal LN | 6,839 | 1.54E+03 |
| Axillary LN | 8,010 | 2.05E+03 |
| Brachial LN | 7,979 | 1.30E+03 |
| LNP Composition 1 | | |
| Liver | 2,024,000 | 1.52E+06 |
| Heart | 61,985 | 2.62E+04 |
| Kidneys | 182,895 | 1.16E+05 |
| Lungs | 302,105 | 4.03E+05 |
| Spleen | 354,350 | 2.41E+05 |
| Inguinal LN | 215,875 | 1.41E+05 |
| Axillary LN | 6,537,000 | 2.07E+06 |
| Brachial LN | 26,760,000 | 2.60E+06 |
| LNP Composition 2 | | |
| Liver | 18,545 | 2.53E+03 |
| Heart | 8,217 | 1.44E+03 |
| Kidneys | 12,167 | 3.51E+03 |
| Lungs | 14,858 | 2.18E+03 |
| Spleen | 9,593 | 1.06E+03 |
| Inguinal LN | 9,355 | 1.38E+03 |
| Axillary LN | 82,165 | 1.19E+05 |
| Brachial LN | 839,068 | 1.21E+06 |
| LNP Composition 3 | | |
| Liver | 34,588 | 1.38E+04 |
| Heart | 7,296 | 8.81E+02 |
| Kidneys | 9,516 | 1.54E+03 |
| Lungs | 16,720 | 5.31E+03 |
| Spleen | 10,922 | 1.62E+03 |
| Inguinal LN | 9,144 | 5.32E+02 |
| Axillary LN | 36,807 | 4.29E+04 |
| Brachial LN | 577,525 | 6.58E+05 |
| LNP Composition 4 | | |
| Liver | 376,625 | 2.02E+05 |
| Heart | 30,893 | 1.33E+04 |
| Kidneys | 74,338 | 2.69E+04 |
| Lungs | 32,865 | 1.68E+04 |
| Spleen | 107,750 | 5.00E+04 |
| Inguinal LN | 55,193 | 6.27E+03 |
| Axillary LN | 3,288,500 | 1.50E+06 |
| Brachial LN | 20,210,000 | 3.96E+06 |
| LNP Composition 5 | | |
| Liver | 92,540 | 1.75E+04 |
| Heart | 21,973 | 9.90E+03 |
| Kidneys | 50,423 | 3.86E+04 |
| Lungs | 26,113 | 6.52E+03 |
| Spleen | 83,038 | 4.52E+04 |
| Inguinal LN | 52,158 | 2.36E+04 |
| Axillary LN | 1,014,325 | 7.90E+05 |
| Brachial LN | 15,703,000 | 6.16E+06 |
| LNP Composition 6 | | |
| Liver | 16,200 | 4.84E+03 |
| Heart | 9,387 | 1.45E+03 |
| Kidneys | 8,914 | 1.50E+03 |
| Lungs | 15,570 | 1.45E+03 |
| Spleen | 9,625 | 7.73E+02 |
| Inguinal LN | 10,046 | 1.65E+03 |
| Axillary LN | 10,744 | 2.01E+03 |
| Brachial LN | 13,160 | 1.77E+03 |
| LNP Composition 7 | | |
| Liver | 11,317 | 2.38E+03 |
| Heart | 8,383 | 9.43E+02 |
| Kidneys | 8,784 | 1.28E+03 |
| Lungs | 13,868 | 7.31E+02 |
| Spleen | 10,687 | 1.22E+03 |
| Inguinal LN | 10,111 | 1.46E+03 |
| Axillary LN | 11,179 | 1.36E+03 |
| Brachial LN | 191,210 | 1.48E+05 |
| LNP Composition 8 | | |
| Liver | 446,568 | 4.19E+05 |
| Heart | 79,578 | 5.01E+04 |

TABLE 2-continued

| Tissue | Ave | SD |
|---|---|---|
| Kidneys | 335,980 | 3.14E+05 |
| Lungs | 49,225 | 3.04E+04 |
| Spleen | 63,665 | 3.91E+04 |
| Inguinal LN | 205,740 | 2.35E+05 |
| Axillary LN | 3,756,300 | 5.51E+06 |
| Brachial LN | 17,844,000 | 8.32E+06 |

Figure 5:
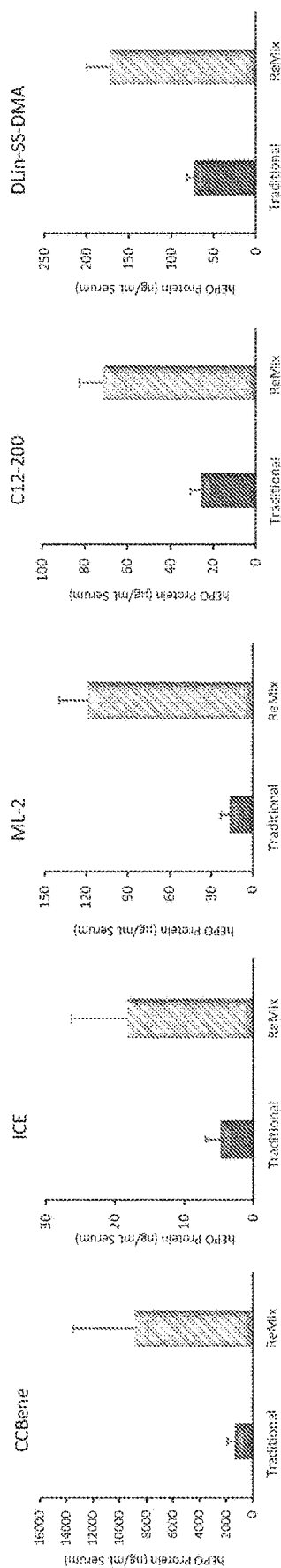
FIG. 5 depicts comparison of remix and traditional methods of liposome formation. Remix compositions lead to higher expression of exemplary hEPO expression in multiple cationic lipid used.
Figure 6:
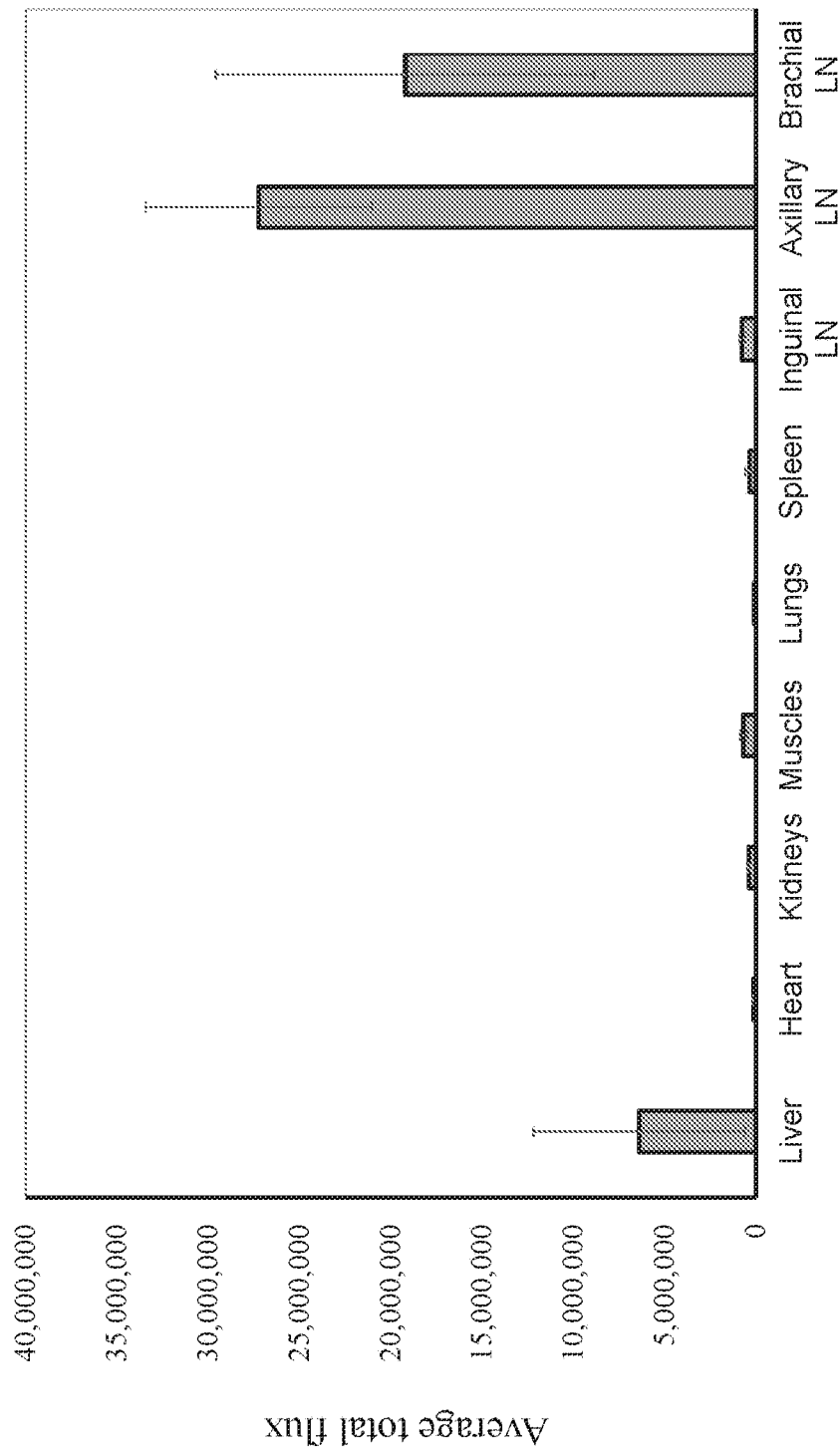
FIG. 6 depicts enriched expression of a Remix formulation in the lymph nodes.

Additionally, an improved LNP formulation process was adapted to increase the potency of the mRNA-LNP expressions in vivo. This process includes a step of heating one or more of the solutions (i.e., applying heat from a heat source to the solution) to a temperature (or to maintain at a temperature) greater than ambient temperature. The solutions comprise a pre-formed lipid nanoparticles, mRNA and the mixed solution comprising the lipid nanoparticle encapsulated mRNA (hereafter, the remix formulation), as outlined in Applicant's prior Application, U.S. Ser. No. 15/809,680, or the corresponding international application, PCT/US17/61113, both were filed on Nov. 10, 2017, and both of which are fully incorporated herein by reference. As shown in FIG. 5 using exemplary hEPO mRNA as a proof of concept using the remix protocol, higher expression of hEPO was observed in multiple cationic lipid compositions compared to the traditional (no heat, unmixed LNP formulations). FIG. 6 shows enrichment of FFL expression in axillary and brachial lymph nodes when delivered as a Remix formulation 24 hours after administration of the mRNA-LNP composition.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of inducing an immune response in vivo comprising:

administering to a subject in need thereof a composition comprising a messenger RNA (mRNA) encoding an antigen, encapsulated in a lipid nanoparticle, at a dosing regimen sufficient to induce an antigen specific T cell response and/or an antigen specific antibody response, wherein the lipid nanoparticle comprises at least one cationic lipid selected from the group consisting of ICE (imidazole cholesterol ester), HGT5001 (15Z, 18Z)-N, N-dimethyl-6-((9Z,12Z)-octadeca-9, 12-dien-1-yl) tetracosa-4, 15, 18-trien-1-amine), and Target 23 (3-(4-(bis (2-hydroxydodecyl) amino)butyl)-6-(4-((2-hydroxydodecyl) (2-hydroxyundecyl)amino)butyl)-1, 4-dioxane-2,5-dione).

2. The method of claim 1, wherein the composition is administered subcutaneously, intradermally, intramuscularly, or intravenously.

3. A method of delivering a vaccine in vivo comprising:
administering to a subject in need thereof a vaccine composition comprising a messenger RNA (mRNA) encoding an antigen, encapsulated in a lipid nanoparticle, wherein the vaccine composition is administered intramuscularly or subcutaneously,
wherein the lipid nanoparticle comprises at least one cationic lipid selected from the group consisting of ICE (imidazole cholesterol ester), HGT5001 (15Z, 18Z)-N, N-dimethyl-6-((9Z,12Z)-octadeca-9,12-dien-1-yl)tetracosa-4,15,18-trien-1-amine), and Target 23 (3-(4-(bis (2-hydroxydodecyl)amino)butyl)-6-(4-((2-hydroxydodecyl)(2-hydroxyundecyl)amino)butyl)-1,4-dioxane-2,5-dione).

4. The method of claim 3, wherein the vaccine composition is administered at a dosing regimen sufficient to induce an antigen specific T cell response and/or an antigen specific antibody response.

5. The method of claim 3, wherein the antigen is a protein or a peptide.

6. The method of claim 4, wherein the dosing regimen comprises injecting a single dose.

7. The method of claim 4, wherein the dosing regimen comprises injecting multiple doses periodically.

8. The method of claim 4, wherein the dosing regimen comprises a dose ranging from 0.1 μg-100 mg mRNA.

9. The method of claim 8, wherein the dose is selected from 0.1 μg, 0.3 μg, 0.5 μg, 1 μg, 5 μg, 10 μg, 25 μg, 50 μg, and 100 μg mRNA.

10. The method of claim 4, wherein the dosing regimen comprises a dose ranging from 0.01 μg-10 mg mRNA per kg body weight.

11. The method of claim 7, wherein each of the multiple doses comprise the same dosage amount of mRNA or a different dosage amount of mRNA.

12. The method of claim 7, wherein each of the multiple doses are injected one week apart, two weeks apart or three weeks apart.

13. The method of claim 7, wherein each of the multiple doses are injected weekly.

14. The method of claim 7, wherein at least two of the multiple doses are injected within 3 weeks.

15. The method of claim 3, wherein the mRNA comprises one or more modified nucleotides.

16. The method of claim 1, wherein the lipid nanoparticle further comprises one or more helper lipids and one or more PEG lipids.

17. The method of claim 16, wherein:
a) the one or more helper lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), and DOPG (1,2-dioleoyl-sn-glycero-3-phospho-(1'-rac-glycerol)), and
b) the one or more PEG lipids are selected from derivatized ceramides; PEG-modified lipids having a polyethylene glycol chain of up to 5 kDa in length covalently attached to a lipid with alkyl chain(s) of C6-C20 length, and a PEGylated cholesterol.

18. The method of claim 3, wherein the administration of the composition results in the expression of the antigen encoded by the mRNA in the lymphocytes of the subject.

* * * * *

SEQUENCE LISTING

```
<160> NUMBER OF SEQ ID NOS: 3

<210> SEQ ID NO 1
<211> LENGTH: 140
<212> TYPE: RNA
<213> ORGANISM: Artificial Sequence
<220> FEATURE:
<223> OTHER INFORMATION: Synthetic Oligonucleotide

<400> SEQUENCE: 1
ggacagaucg ccuggagacg ccauccacgc uguuuugacc uccauagaag acaccgggac     60
cgauccagcc uccgcggccg ggaacggugc auuggaacgc ggauucgccg ugccaagagu    120
gacucaccgu ccuugacacg                                                140

<210> SEQ ID NO 2
<211> LENGTH: 105
<212> TYPE: RNA
<213> ORGANISM: Artificial Sequence
<220> FEATURE:
<223> OTHER INFORMATION: Synthetic Oligonucleotide

<400> SEQUENCE: 2
cggguggcau cccugugacc ccuccccagu gccucuccug gcccuggaag uugccacucc     60
agugcccacc agccuugucc uaauaaaauu aaguugcauc aagcu                    105

<210> SEQ ID NO 3
<211> LENGTH: 105
<212> TYPE: RNA
<213> ORGANISM: Artificial Sequence
<220> FEATURE:
<223> OTHER INFORMATION: Synthetic Oligonucleotide

<400> SEQUENCE: 3
ggguggcauc ccugugaccc cuccccagug ccucuccugg cccuggaagu ugccacucca     60
gugcccacca gccuuguccu aauaaaauua aguugcauca aagcu                    105
```